US009260496B2

(12) United States Patent
Dasgupta et al.

(10) Patent No.: US 9,260,496 B2
(45) Date of Patent: Feb. 16, 2016

(54) FIBRONECTIN BASED SCAFFOLD DOMAIN PROTEINS THAT BIND IL-23

(75) Inventors: Ruchira Dasgupta, Auburndale, MA (US); Steven Sheriff, Princeton, NJ (US); Anzhi Wei, Newtown, PA (US); Vidhyashankar Ramamurthy, North Wales, PA (US); Alex Bush, Brighton, MA (US); Katie A. Russo, Watertown, MA (US); Linda Engle, Framingham, MA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 13/995,356

(22) PCT Filed: Dec. 20, 2011

(86) PCT No.: PCT/US2011/065974
§ 371 (c)(1),
(2), (4) Date: Jun. 18, 2013

(87) PCT Pub. No.: WO2012/088006
PCT Pub. Date: Jun. 28, 2012

(65) Prior Publication Data
US 2013/0288372 A1 Oct. 31, 2013

Related U.S. Application Data

(60) Provisional application No. 61/426,024, filed on Dec. 22, 2010.

(51) Int. Cl.
*C07K 14/47* (2006.01)
*C07K 14/78* (2006.01)
*C07K 16/24* (2006.01)
*A61K 38/00* (2006.01)

(52) U.S. Cl.
CPC .............. *C07K 14/4703* (2013.01); *C07K 14/78* (2013.01); *C07K 16/244* (2013.01); *A61K 38/00* (2013.01); *C07K 2317/34* (2013.01); *C07K 2317/76* (2013.01); *C07K 2317/92* (2013.01); *C07K 2318/20* (2013.01); *C07K 2319/02* (2013.01); *C07K 2319/30* (2013.01); *C07K 2319/31* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 5,631,144 A | 5/1997 | Lemoine et al. | |
| 6,207,446 B1 | 3/2001 | Szostak et al. | |
| 6,214,553 B1 | 4/2001 | Szostak et al. | |
| 6,258,558 B1 | 7/2001 | Szostak et al. | |
| 6,261,804 B1 | 7/2001 | Szostak et al. | |
| 6,281,344 B1 | 8/2001 | Szostak et al. | |
| 6,518,018 B1 | 2/2003 | Szostak et al. | |
| 6,559,126 B2 | 5/2003 | Tournaire et al. | |
| 6,818,418 B1 | 11/2004 | Lipovsek et al. | |
| 7,115,396 B2 * | 10/2006 | Lipovsek ............... | C07K 14/47 435/69.1 |
| 2005/0287153 A1 | 12/2005 | Dennis | |
| 2007/0003549 A1 | 1/2007 | Ignatovich et al. | |
| 2007/0048282 A1 | 3/2007 | Rosen et al. | |
| 2007/0178082 A1 | 8/2007 | Silence et al. | |
| 2007/0269422 A1 | 11/2007 | Beirnaert et al. | |

FOREIGN PATENT DOCUMENTS

| | | |
|---|---|---|
| WO | WO9411026 | 5/1994 |
| WO | WO0204523 A2 | 1/2002 |
| WO | WO2009068649 A2 | 6/2009 |
| WO | WO2011103105 A1 | 8/2011 |

OTHER PUBLICATIONS

RCSB Protein Data Bank—1TTG. http://www.rcsb.org/pdg/explore/remediatedSequence.do?structureId=1TTG&bionumber=1. 2014.*
Aggarwal, et al., Interleukin-23 Promotes a Distinct CD4 T Cell Activation State Characterized by the Production of Interleukin-17, J. Biol. Chem., vol. 278 (3), pp. 1910-1914 (2003).
Batori, et al., "Exploring the potential of the monobody scaffold: effects of loop elongation on the stability of a fibronectin type III domain", Protein Engineering, vol. 15 (12), pp. 1015-1020 (2002).
Berman, et al., "The Protein Data Bank", Nucleic Acids Res., vol. 28 (1), pp. 235-242 (2000).
Berman, et al., "Announcing the Worldwide Protein Data Bank, Nature Structure Biology, "vol. 10 (12), pp. 980 (2003).
Beyer, et al., "Crystal Structures of the Pro-Inflammatory Cytokine Interleukin-23 and Its Complex with a High-Affinity Neutralizing Antibody", J. Mol. Biol., vol. 382, pp. 942-955 (2008).
Collaborative Computational Project, No. 4, SERC Daresbury Laboratory, Warrington, WA44AD, England, The CCP4 Suite: Programs for Protein Cystallography, Acta Cryst., vol. D50, pp. 760-763 (1994).
Connell, Nancy D., "Expression systems for use in actinomycetes and related organisms", Curr. Opin. Biotech., vol. 12, pp. 446-449 (2001).
Connolly, Michael L., "Analytical Molecular Surface Calculation", J. Appl. Cryst., vol. 16, pp. 548-558 (1983).
Emsley, et al., "Features and development of Coot", Acta Cryst., vol. D66, pp. 486-501 (2010).
Emsley, et al., "Coot: model-building tools for molecular graphics", Acta Cryst., vol. D60, pp. 2126-2132 (2004).
Gelin et al., "Side-Chain Torsional Potentials: Effect of Dipeptide, Protein, and Solvent Environment", Biochemistry, vol. 18 (7) pp. 1256-1268 (1979).
Koide, et al., "The Importance of Being Tyrosine: Lessons in Molecular Recognition from Minimalist Synthetic Binding Proteins", ACS Chem. Biology, vol. 4(5), pp. 325-334 (2009).

(Continued)

*Primary Examiner* — Amber D Steele
*Assistant Examiner* — Schuyler Milton
(74) *Attorney, Agent, or Firm* — Nickki Parlet

(57) ABSTRACT

The present invention relates to fibronectin based scaffold domain protein that bind interleukin 23 (IL-23). The invention also relates to the use of the innovative proteins in therapeutic applications to treat autoimmune diseases. The invention further relates to cells comprising such proteins, polynucleotide encoding such proteins or fragments thereof, and to vectors comprising the polynucleotides encoding the innovative proteins.

4 Claims, 8 Drawing Sheets

(56) References Cited

OTHER PUBLICATIONS

Koide, et al., "Stabilization of a Fibronectin Type III Domain by the Removal of Unfavorable Electrostatic Interactions on the Protein Surface", Biochem., vol. 40, pp. 10326-10333 (2001).
Kossiakoff, et al., "Understanding mechanisms governing protein-protein interactions from synthetic binding interfaces", Curr. Opin. Structural Biol., vol. 18, pp. 499-506 (2008).
Krystek, et al., "Affinity and Specificity of Serine Endopeptidase-Protein Inhibitor Interactions", J. Mol. Biol., vol. 234, pp. 661-679 (1993).
Lawrence, et al., "Shape Complementarity at Protein/Protein Interfaces", J. Mol. Biol., vol. 234, pp. 946-950 (1993).
Luckow, et al., "Trends in the Development of Baculovirus Expression Vectors", Biotechnology, vol. 6, pp. 47-55 (1988).
Makrides, Savvas C., Strategies for Achieving High-Level Expression of Genes in *Escherichia coli*, Microbiological Reviews, vol. 60 (3), pp. 512-538 (1996).
Mayfield, et al., "Expression and assembly of a fully active antibody in algae", PNAS, vol. 100 (2), pp. 438-442 (2003).
McCoy, et al., "Phaser crystallographic software", J. Appl. Cryst., vol. 40, pp. 658-674 (2007).
Mian, et al., "Structure, Function and Properties of Antibody Binding Sites", J. Mol. Biol., vol. 217, pp. 133-151 (1991).
Navaza, et al., "On the Fast Translation Functions for Molecular Replacement", Acta Cryst., vol. A51, pp. 445-449 (1995).
Navaza, J., "AMoRe: an Automated Package for Molecular Replacement", Acta Cryst., vol. A50, pp. 157-163 (1994).
Novotny, et al., "On the Attribution of Binding Energy in Antigen-Antibody Complexes McPC 603, D1.3, and HyHEL-5", Biochem., vol. 28, pp. 4735-4749 (1989).
Padlan, Eduardo A., "On the Nature of Antibody Combining Sites: Unusual Structural Features That May Confer on These Sites an Enhanced Capacity for Binding Ligands", Proteins: Structure, Function, and Genetics, vol. 7, pp. 112-124 (1990).
Parham, et al., "A Receptor for the Heterodimeric Cytokine IL-23 is Composed of IL-12Rβ1 and a Novel Cytokine Receptor Subunit, IL-23R", J. Immunology, vol. 168, pp. 5699-5708 (2002).
Pflugraph, et al., "The finer things in X-ray diffraction data collection", Acta Cryst., vol. D55, pp. 1718-1725 (1999).
Ramamurthy, et al., "Structures of Adnectin/Protein Complexes Reveal an Expanded Binding Footprint", Structure, vol. 20, pp. 259-269 (2012).
Roberts, et al., "RNA-peptide fusions for the in vitro selection of peptides and proteins", PNAS, vol. 94, pp. 12297-12302 (1997).
Sharp, et al., "Synonymous Codon Usage in *Saccharomyces cerevisiae*", Yeast, vol. 7, pp. 657-678 (1991).
Sheriff, et al., "Structure of Myohemerythrin in the Azidomet State at 1•7/1•3 Å Resolution", J. Mol Biol., vol. 197, pp. 273-296 (1987).
Sheriff, Steven, "Some Methods for Examining the Interactions between Two Molecules", Immunomethods, vol. 3, pp. 191-196 (1993).
Sheriff, et al., "Implementation of a six-dimentional search using the AMoRe translation function for difficult molecular-replacement problems", J. App. Cryst., vol. 32, pp. 98-101 (1999).
Sinclair, et al., "Synonymous codon usage bias and the expression of human glucocerebrosidase in the methylotrophic yeast, *Pichia pastoris*", Protein Expression and Purification, vol. 26, pp. 96-105 (2002).
Xu, et al., "Directed Evolution of High-Affinity Antibody Mimics Using mRNA Display", Chem. & Biol., vol. 9, pp. 933-942 (2002).
Yaniv, Moshe, "Enhancing elements for activation of eurkaryotic promoters", Nature, vol. 297, pp. 17-18 (1982).
PCT International Search Report—Dated Apr. 12, 2012, International Filing Date—Dec. 20, 2011 (6 pages).

* cited by examiner

FIG. 1a

1454D02 (SEQ ID NO:27)
MGVSDVPRDLEVVAATPTSLLISWDHDYPYRRYYRITYGETGGNSPVQEFTVPRNIN
TATISGLKPGVDYTITVYAVTSSYKYDMQYSPISINYRTEIDKPSQHHHHHH

1454C03 (SEQ ID NO:28)
MGVSDVPRDLEVVAATPTSLLISWDMYYPYSRYYRITYGETGGNSPVQEFTVPKEYD
TATISGLKPGVDYTITVYAVTSSYKYDMQYSPISINYRTEIDKPSQHHHHHH

1454B05 (SEQ ID NO:29)
MGVSDVPRDLEVVAATPTSLLISWYHDYPYRRYYRITYGETGGNSPVQEFTVPKDEE
TATISGLKPGVDYTITVYAVTSSYKYDMQYSPISINYRTEIDKPSQHHHHHH

1454F05 (SEQ ID NO:30)
MGVSDVPRDLEVVAATPTSLLISWYMHYPYSRYYRITYGETGGNSPVQEFTVPKQHD
TATISGLKPGVDYTITVYAVTSSYKYDMQYSPISINYRTEIDKPSQHHHHHH

1454F07 (SEQ ID NO:31)
MGVSDVPRDLEVVAATPTSLLISWYHMYSYRRYYRITYGETGGNSPVQEFTVPRDVD
TATISGLKPGVDYTITVYAVTSSYKYDMQYSPISINYRTEIDKPSQHHHHHH

1454B08 (SEQ ID NO:32)
MGVSDVPRDLEVVAATPTSLLISWEHDYPYRRYYRITYGETGGNSPVQEFTVPKDVD
TATISGLKPGVDYTITVYAVTSSYKYDMQYSPISINYRTEIDKPSQHHHHHH

1454E09 (SEQ ID NO:33)
MGVSDVPRDLEVVAATPTSLLISWMHDYPYRRYYRITYGETGGNSPVQEFTVPMEED
TATISGLKPGVDYTITVYAVTSSYKYDMQYSPISINYRTEIDKPSQHHHHHH

1454F09 (SEQ ID NO:34)
MGVSDVPRDLEVVAATPTSLLISWDHNYSYRRYYRITYGETGGNSPVQEFTVPRHTD
TATISGLKPGVDYTITVYAVTSSYKYDMQYSPISINYRTEIDKPSQHHHHHH

1454H11 (SEQ ID NO:35)
MGVSDVPRDLEVVAATPTSLLISWEHDYPYRRYYRITYGETGGNSPVQEFTVPREDS
TATISGLKPGVDYTITVYAVTSSYKYDMQYSPISINYRTEIDKPSQHHHHHH

1241A05 (SEQ ID NO:36)
MGVSDVPRDLEVVAATPTSLLISWNHNYSYRYYRITYGETGGNSPVQEFTVPRGVA
TATISGLKPGVDYTITVYAVTSSYKYDMQYSPISINYRTEIDKPSQHHHHHH

1866C02 (SEQ ID NO:37)
MGVSDVPRDLEVVAATPTSLLISWDHNYTWYRYYRITYGETGGNSPVQEFTVPRGVD
TATISGLKPGVDYTITVYAVTSSYKYDIQYPPISINYRTEIDKPSQHHHHHH

FIG. 1b

1866D11 (SEQ ID NO:38)
MGVSDVPRDLEVVAATPTSLLISWDHDYPYRRYYRITYGETGGNSPVQEFTVPKDVD
TATISGLKPGVDYTITVYAVTSSYKYDIQYPPISINYRTEIDKPSQHHHHHH

1866F10 (SEQ ID NO:39)
MGVSDVPRDLEVVAATPTSLLISWDHDYPYRRYYRITYGETGGNSPVQEFTVPRNIN
TATISGLKPGVDYTITVYAVTSTLKYDIQYSPISINYRTEIDKPSQHHHHHH

FIG. 2a

1454D02 (SEQ ID NO:40)
ATGGGAGTTTCTGATGTGCCGCGCGACCTGGAAGTGGTTGCTGCCACCCCCACCAGC
CTGCTGATCAGCTGGGACCATGACTACCCGTACCGTCGATATTACCGCATCACTTAC
GGCGAAACAGGAGGCAATAGCCCTGTCCAGGAGTTCACTGTGCCTCGTAACATCAAC
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

1454C03 (SEQ ID NO:41)
ATGGGAGTTTCTGATGTGCCGCGCGACCTGGAAGTGGTTGCTGCCACCCCCACCAGC
CTGCTGATCAGCTGGGACATGTACTACCCGTACTCTCGATATTACCGCATCACTTAC
GGCGAAACAGGAGGCAATAGCCCTGTCCAGGAGTTCACTGTGCCTAAAGAATACGAC
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

1454B05 (SEQ ID NO:42)
ATGGGAGTTTCTGATGTGCCGCGCGACCTGGAAGTGGTTGCTGCCACCCCCACCAGC
CTGCTGATCAGCTGGTACCATGACTACCCGTACCGTCGATATTACCGCATCACTTAC
GGCGAAACAGGAGGCAATAGCCCTGTCCAGGAGTTCACTGTGCCTAAAGACGAAGAA
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

1454F05 (SEQ ID NO:43)
ATGGGAGTTTCTGATGTGCCGCGCGACCTGGAAGTGGTTGCTGCCACCCCCACCAGC
CTGCTGATCAGCTGGTACATGCATTACCCGTACTCTCGATATTACCGCATCACTTAC
GGCGAAACAGGAGGCAATAGCCCTGTCCAGGAGTTCACTGTGCCTAAACAGCATGAC
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

1454F07 (SEQ ID NO:44)
ATGGGAGTTTCTGATGTGCCGCGCGACCTGGAAGTGGTTGCTGCCACCCCCACCAGC
CTGCTGATCAGCTGGTACCATATGTACTCTTACCGTCGATATTACCGCATCACTTAC
GGCGAAACAGGAGGCAATAGCCCTGTCCAGGAGTTCACTGTGCCTCGTGACGTTGAC
ACAGCTACCATAAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

FIG. 2b

1454B08 (SEQ ID NO:45)
ATGGGAGTTTCTGATGTGCCGCGCGACCTGGAAGTGGTTGCTGCCACCCCCACCAGC
CTGCTGATCAGCTGGGAACATGACTACCCGTACCGTCGATATTACCGCATCACTTAC
GGCGAAACAGGAGGCAATAGCCCTGTCCAGGAGTTCACTGTGCCTAAAGACGTTGAC
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

1454E09 (SEQ ID NO:46)
ATGGGAGTTTCTGATGTGCCGCGCGACCTGGAAGTGGTTGCTGCCACCCCCACCAGC
CTGCTGATCAGCTGGATGCATGACTACCCGTACCGTCGATATTACCGCATCACTTAC
GGCGAAACAGGAGGCAATAGCCCTGTCCAGGAGTTCACTGTGCCTATGGAAGAAGAC
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

1454F09 (SEQ ID NO:47)
ATGGGAGTTTCTGATGTGCCGCGCGACCTGGAAGTGGTTGCTGCCACCCCCACCAGC
CTGCTGATCAGCTGGGACCATAACTACTCTTACCGTCGATATTACCGCATCACTTAC
GGCGAAACAGGAGGCAATAGCCCTGTCCAGGAGTTCACTGTGCCTCGTCATACTGAC
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

1454H11 (SEQ ID NO:48)
ATGGGAGTTTCTGATGTGCCGCGCGACCTGGAAGTGGTTGCTGCCACCCCCACCAGC
CTGCTGATCAGCTGGGAACATGACTACCCGTACCGTCGATATTACCGCATCACTTAC
GGCGAAACAGGAGGCAATAGCCCTGTCCAGGAGTTCACTGTGCCTCGTGAAGACTCT
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

1241A05 (SEQ ID NO:49)
ATGGGAGTTTCTGATGTGCCGCGCGACCTGGAAGTGGTTGCTGCCACCCCCACCAGC
CTGCTGATCAGCTGGAACCATAACTACTCTTACTACCGATATTACCGCATCACTTAC
GGCGAAACAGGAGGCAATAGCCCTGTCCAGGAGTTCACTGTGCCTCGTGGAGTTGCT
ACAGCTACCATCAGCGGCCTTAAACCTGGCGTTGATTATACCATCACTGTGTATGCT
GTCACTTCTTCTTACAAATACGACATGCAGTACTCTCCAATTTCCATTAATTACCGC
ACAGAAATTGACAAACCATCCCAGCACCATCACCACCACCACTGA

FIG. 2c

1866C02 (SEQ ID NO:50)
ATGGGAGTTTCTGATGTGCCGCGCGACCTGGAAGTGGTTGCTGCCACCCCCACCAGC
CTGCTGATCAGCTGGGACCATAACTACACTTGGTATCGATATTACCGCATCACTTAC
GGCGAAACAGGAGGCAATAGCCCTGTCCAGGAGTTCACTGTGCCTCGTGGAGTTGAT
ACAGCTACCATCAGCGGCCTTAAACCTGGCGTTGATTATACCATCACTGTGTATGCT
GTCACTTCTTCTTACAAGTACGACATTCAGTACCCGCCAATTTCCATTAATTACCGC
ACAGAAATTGACAAACCATCCCAGCACCATCACCACCACCACTGA

1866D11 (SEQ ID NO:51)
ATGGGAGTTTCTGATGTGCCGCGCGACCTGGAAGTGGTTGCTGCCACCCCCACCAGC
CTGCTGATCAGCTGGGACCATGACTACCCGTACCGTCGATATTACCGCATCACTTAC
GGCGAAACAGGAGGCAATAGCCCTGTCCAGGAGTTCACTGTGCCTAAAGACGTTGAC
ACAGCTACCATCAGCGGCCTTAAACCTGGCGTTGATTATACCATCACTGTGTATGCT
GTCACTTCGTCTTACAAATACGACATTCAATACCCACCAATTTCCATTAATTACCGC
ACAGAAATTGACAAACCATCCCAGCACCATCACCACCACCACTGA

1866F10 (SEQ ID NO:52)
ATGGGAGTTTCTGATGTGCCGCGCGACCTGGAAGTGGTTGCTGCCACCCCCACCAGC
CTGCTGATCAGCTGGGACCATGACTACCCGTACCGTCGATATTACCGCATCACTTAC
GGCGAAACAGGAGGCAATAGCCCTGTCCAGGAGTTCACTGTGCCTCGTAACATCAAC
ACAGCTACCATCAGCGGCCTTAAACCTGGCGTTGATTATACCATCACTGTGTATGCT
GTCACTTCGACTTTAAAATACGACATTCAGTATTCTCCAATTTCCATTAATTACCGC
ACAGAAATTGACAAACCATCCCAGCACCATCACCACCACCACTGA

FIG. 5
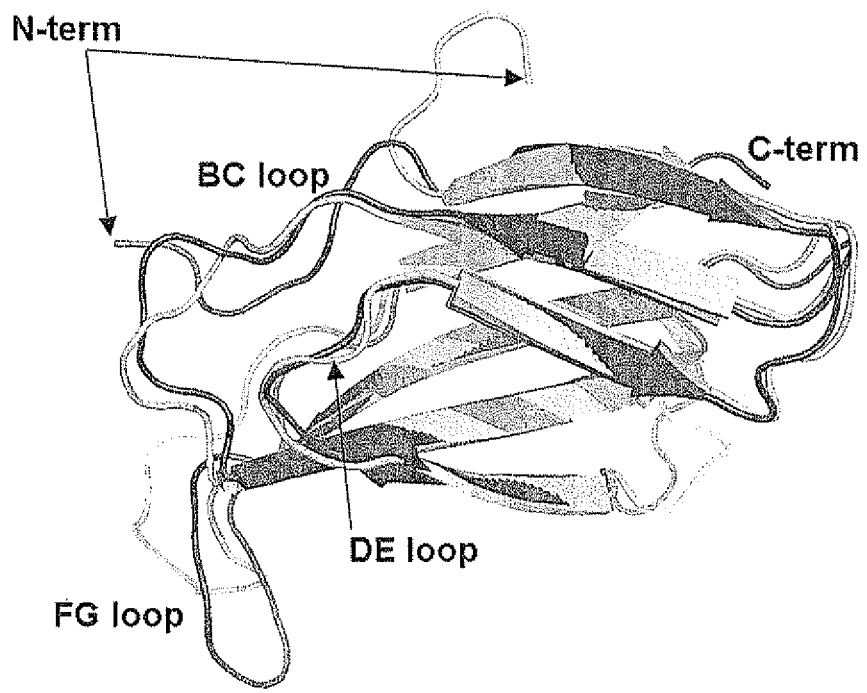
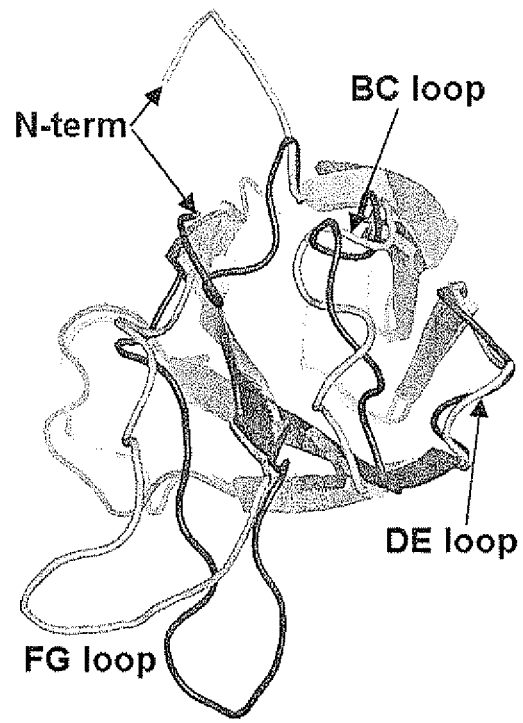

SEQUENCE LISTING

```
<160> NUMBER OF SEQ ID NOS: 52

<210> SEQ ID NO 1
<211> LENGTH: 94
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 7
<212> TYPE: PRT
<213> ORGANISM: Homo sapiens
<220> FEATURE:
<221> NAME/KEY: MISC_FEATURE
<223> OTHER INFORMATION: BC Loop

<400> SEQUENCE: 2

Asp His Asp Tyr Pro Tyr Arg
1               5

<210> SEQ ID NO 3
<211> LENGTH: 7
<212> TYPE: PRT
<213> ORGANISM: Homo sapiens
<220> FEATURE:
<221> NAME/KEY: MISC_FEATURE
<223> OTHER INFORMATION: BC Loop

<400> SEQUENCE: 3
```

Asp Met Tyr Tyr Pro Tyr Ser
1               5

<210> SEQ ID NO 4
<211> LENGTH: 7
<212> TYPE: PRT
<213> ORGANISM: Homo sapiens
<220> FEATURE:
<221> NAME/KEY: MISC_FEATURE
<223> OTHER INFORMATION: BC Loop

<400> SEQUENCE: 4

Tyr His Asp Tyr Pro Tyr Arg
1               5

<210> SEQ ID NO 5
<211> LENGTH: 7
<212> TYPE: PRT
<213> ORGANISM: Homo sapiens
<220> FEATURE:
<221> NAME/KEY: MISC_FEATURE
<223> OTHER INFORMATION: BC Loop

<400> SEQUENCE: 5

Tyr Met His Tyr Pro Tyr Ser
1               5

<210> SEQ ID NO 6
<211> LENGTH: 7
<212> TYPE: PRT
<213> ORGANISM: Homo sapiens
<220> FEATURE:
<221> NAME/KEY: MISC_FEATURE
<223> OTHER INFORMATION: BC Loop

<400> SEQUENCE: 6

Tyr His Met Tyr Ser Tyr Arg
1               5

<210> SEQ ID NO 7
<211> LENGTH: 7
<212> TYPE: PRT
<213> ORGANISM: Homo sapiens
<220> FEATURE:
<221> NAME/KEY: MISC_FEATURE
<223> OTHER INFORMATION: BC Loop

<400> SEQUENCE: 7

Glu His Asp Tyr Pro Tyr Arg
1               5

<210> SEQ ID NO 8
<211> LENGTH: 7
<212> TYPE: PRT
<213> ORGANISM: Homo sapiens
<220> FEATURE:
<221> NAME/KEY: MISC_FEATURE
<223> OTHER INFORMATION: BC Loop

<400> SEQUENCE: 8

Met His Asp Tyr Pro Tyr Arg
1               5

<210> SEQ ID NO 9
<211> LENGTH: 7
<212> TYPE: PRT
<213> ORGANISM: Homo sapiens
<220> FEATURE:

```
<221> NAME/KEY: MISC_FEATURE
<223> OTHER INFORMATION: BC Loop

<400> SEQUENCE: 9

Asp His Asn Tyr Ser Tyr Arg
1               5

<210> SEQ ID NO 10
<211> LENGTH: 7
<212> TYPE: PRT
<213> ORGANISM: Homo sapiens

<400> SEQUENCE: 10

Asn His Asn Tyr Ser Tyr Tyr
1               5

<210> SEQ ID NO 11
<211> LENGTH: 7
<212> TYPE: PRT
<213> ORGANISM: Homo sapiens
<220> FEATURE:
<221> NAME/KEY: MISC_FEATURE
<223> OTHER INFORMATION: BC Loop

<400> SEQUENCE: 11

Asp His Asn Tyr Thr Trp Tyr
1               5

<210> SEQ ID NO 12
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 12

Arg Asn Ile Asn
1

<210> SEQ ID NO 13
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 13

Lys Glu Tyr Asp
1

<210> SEQ ID NO 14
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 14

Lys Asp Glu Glu
1

<210> SEQ ID NO 15
<211> LENGTH: 4
<212> TYPE: PRT
```

```
<213> ORGANISM: Homo sapiens
<220> FEATURE:
<221> NAME/KEY: MISC_FEATURE
<223> OTHER INFORMATION: DE Loop

<400> SEQUENCE: 15

Lys Gln His Asp
1

<210> SEQ ID NO 16
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 16

Arg Asp Val Asp
1

<210> SEQ ID NO 17
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 17

Lys Asp Val Asp
1

<210> SEQ ID NO 18
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 18

Met Glu Glu Asp
1

<210> SEQ ID NO 19
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 19

Arg His Thr Asp
1

<210> SEQ ID NO 20
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 20

Arg Glu Asp Ser
1
```

<210> SEQ ID NO 21
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 21

Arg Gly Val Ala
1

<210> SEQ ID NO 22
<211> LENGTH: 4
<212> TYPE: PRT
<213> ORGANISM: Homo sapiens
<220> FEATURE:
<221> NAME/KEY: MISC_FEATURE
<223> OTHER INFORMATION: DE Loop

<400> SEQUENCE: 22

Arg Gly Val Asp
1

<210> SEQ ID NO 23
<211> LENGTH: 10
<212> TYPE: PRT
<213> ORGANISM: Homo sapiens
<220> FEATURE:
<221> NAME/KEY: MISC_FEATURE
<223> OTHER INFORMATION: FG Loop

<400> SEQUENCE: 23

Ser Ser Tyr Lys Tyr Asp Met Gln Tyr Ser
1               5                   10

<210> SEQ ID NO 24
<211> LENGTH: 10
<212> TYPE: PRT
<213> ORGANISM: Homo sapiens
<220> FEATURE:
<221> NAME/KEY: MISC_FEATURE
<223> OTHER INFORMATION: FG Loop

<400> SEQUENCE: 24

Ser Ser Tyr Lys Tyr Asp Ile Gln Tyr Pro
1               5                   10

<210> SEQ ID NO 25
<211> LENGTH: 10
<212> TYPE: PRT
<213> ORGANISM: Homo sapiens
<220> FEATURE:
<221> NAME/KEY: MISC_FEATURE
<223> OTHER INFORMATION: FG Loop

<400> SEQUENCE: 25

Ser Thr Leu Lys Tyr Asp Ile Gln Tyr Ser
1               5                   10

<210> SEQ ID NO 26
<211> LENGTH: 4
<212> TYPE: PRT
<213> ORGANISM: Homo sapiens
<220> FEATURE:
<221> NAME/KEY: MISC_FEATURE
<223> OTHER INFORMATION: Cysteine linker

```
<400> SEQUENCE: 26

Gly Ser Gly Cys
1

<210> SEQ ID NO 27
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1454D02

<400> SEQUENCE: 27

Met Gly Val Ser Asp Val Pro Arg Asp Leu Glu Val Val Ala Ala Thr
1               5                   10                  15

Pro Thr Ser Leu Leu Ile Ser Trp Asp His Asp Tyr Pro Tyr Arg Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Asn Ile Asn Thr Ala Thr Ile Ser Gly Leu
    50                  55                  60

Lys Pro Gly Val Asp Tyr Thr Ile Thr Val Tyr Ala Val Thr Ser Ser
65                  70                  75                  80

Tyr Lys Tyr Asp Met Gln Tyr Ser Pro Ile Ser Ile Asn Tyr Arg Thr
                85                  90                  95

Glu Ile Asp Lys Pro Ser Gln His His His His His
            100                 105

<210> SEQ ID NO 28
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1454C03

<400> SEQUENCE: 28

Met Gly Val Ser Asp Val Pro Arg Asp Leu Glu Val Val Ala Ala Thr
1               5                   10                  15

Pro Thr Ser Leu Leu Ile Ser Trp Asp Met Tyr Tyr Pro Tyr Ser Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Glu Tyr Asp Thr Ala Thr Ile Ser Gly Leu
    50                  55                  60

Lys Pro Gly Val Asp Tyr Thr Ile Thr Val Tyr Ala Val Thr Ser Ser
65                  70                  75                  80

Tyr Lys Tyr Asp Met Gln Tyr Ser Pro Ile Ser Ile Asn Tyr Arg Thr
                85                  90                  95

Glu Ile Asp Lys Pro Ser Gln His His His His His
            100                 105

<210> SEQ ID NO 29
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1454B05
```

<400> SEQUENCE: 29

Met Gly Val Ser Asp Val Pro Arg Asp Leu Glu Val Val Ala Ala Thr
1               5                   10                  15

Pro Thr Ser Leu Leu Ile Ser Trp Tyr His Asp Tyr Pro Tyr Arg Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asp Glu Thr Ala Thr Ile Ser Gly Leu
50                  55                  60

Lys Pro Gly Val Asp Tyr Thr Ile Thr Val Tyr Ala Val Thr Ser Ser
65                  70                  75                  80

Tyr Lys Tyr Asp Met Gln Tyr Ser Pro Ile Ser Ile Asn Tyr Arg Thr
                85                  90                  95

Glu Ile Asp Lys Pro Ser Gln His His His His His
                100                 105

<210> SEQ ID NO 30
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1454F05

<400> SEQUENCE: 30

Met Gly Val Ser Asp Val Pro Arg Asp Leu Glu Val Val Ala Ala Thr
1               5                   10                  15

Pro Thr Ser Leu Leu Ile Ser Trp Tyr Met His Tyr Pro Tyr Ser Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Gln His Asp Thr Ala Thr Ile Ser Gly Leu
50                  55                  60

Lys Pro Gly Val Asp Tyr Thr Ile Thr Val Tyr Ala Val Thr Ser Ser
65                  70                  75                  80

Tyr Lys Tyr Asp Met Gln Tyr Ser Pro Ile Ser Ile Asn Tyr Arg Thr
                85                  90                  95

Glu Ile Asp Lys Pro Ser Gln His His His His His
                100                 105

<210> SEQ ID NO 31
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1454F07

<400> SEQUENCE: 31

Met Gly Val Ser Asp Val Pro Arg Asp Leu Glu Val Val Ala Ala Thr
1               5                   10                  15

Pro Thr Ser Leu Leu Ile Ser Trp Tyr His Met Tyr Ser Tyr Arg Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Val Asp Thr Ala Thr Ile Ser Gly Leu
50                  55                  60

Lys Pro Gly Val Asp Tyr Thr Ile Thr Val Tyr Ala Val Thr Ser Ser

-continued

```
                65                  70                  75                  80
Tyr Lys Tyr Asp Met Gln Tyr Ser Pro Ile Ser Ile Asn Tyr Arg Thr
                    85                  90                  95
Glu Ile Asp Lys Pro Ser Gln His His His His His His
                100                 105

<210> SEQ ID NO 32
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1454B08

<400> SEQUENCE: 32

Met Gly Val Ser Asp Val Pro Arg Asp Leu Glu Val Val Ala Ala Thr
1               5                   10                  15
Pro Thr Ser Leu Leu Ile Ser Trp Glu His Asp Tyr Pro Tyr Arg Arg
                20                  25                  30
Tyr Tyr Arg Ile Thr Tyr Gly Glu Thr Gly Gly Asn Ser Pro Val Gln
                35                  40                  45
Glu Phe Thr Val Pro Lys Asp Val Asp Thr Ala Thr Ile Ser Gly Leu
        50                  55                  60
Lys Pro Gly Val Asp Tyr Thr Ile Thr Val Tyr Ala Val Thr Ser Ser
65                  70                  75                  80
Tyr Lys Tyr Asp Met Gln Tyr Ser Pro Ile Ser Ile Asn Tyr Arg Thr
                    85                  90                  95
Glu Ile Asp Lys Pro Ser Gln His His His His His His
                100                 105

<210> SEQ ID NO 33
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1454E09

<400> SEQUENCE: 33

Met Gly Val Ser Asp Val Pro Arg Asp Leu Glu Val Val Ala Ala Thr
1               5                   10                  15
Pro Thr Ser Leu Leu Ile Ser Trp Met His Asp Tyr Pro Tyr Arg Arg
                20                  25                  30
Tyr Tyr Arg Ile Thr Tyr Gly Glu Thr Gly Gly Asn Ser Pro Val Gln
                35                  40                  45
Glu Phe Thr Val Pro Met Glu Glu Asp Thr Ala Thr Ile Ser Gly Leu
        50                  55                  60
Lys Pro Gly Val Asp Tyr Thr Ile Thr Val Tyr Ala Val Thr Ser Ser
65                  70                  75                  80
Tyr Lys Tyr Asp Met Gln Tyr Ser Pro Ile Ser Ile Asn Tyr Arg Thr
                    85                  90                  95
Glu Ile Asp Lys Pro Ser Gln His His His His His His
                100                 105

<210> SEQ ID NO 34
<211> LENGTH: 109
<212> TYPE: PRT
<213> ORGANISM: Homo sapiens
<220> FEATURE:
<221> NAME/KEY: MISC_FEATURE
```

<223> OTHER INFORMATION: 1454F09

<400> SEQUENCE: 34

Met Gly Val Ser Asp Val Pro Arg Asp Leu Glu Val Val Ala Ala Thr
1               5                   10                  15

Pro Thr Ser Leu Leu Ile Ser Trp Asp His Asn Tyr Ser Tyr Arg Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg His Thr Asp Thr Ala Thr Ile Ser Gly Leu
    50                  55                  60

Lys Pro Gly Val Asp Tyr Thr Ile Thr Val Tyr Ala Val Thr Ser Ser
65                  70                  75                  80

Tyr Lys Tyr Asp Met Gln Tyr Ser Pro Ile Ser Ile Asn Tyr Arg Thr
                85                  90                  95

Glu Ile Asp Lys Pro Ser Gln His His His His His His
            100                 105

<210> SEQ ID NO 35
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1454H11

<400> SEQUENCE: 35

Met Gly Val Ser Asp Val Pro Arg Asp Leu Glu Val Val Ala Ala Thr
1               5                   10                  15

Pro Thr Ser Leu Leu Ile Ser Trp Glu His Asp Tyr Pro Tyr Arg Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Glu Asp Ser Thr Ala Thr Ile Ser Gly Leu
    50                  55                  60

Lys Pro Gly Val Asp Tyr Thr Ile Thr Val Tyr Ala Val Thr Ser Ser
65                  70                  75                  80

Tyr Lys Tyr Asp Met Gln Tyr Ser Pro Ile Ser Ile Asn Tyr Arg Thr
                85                  90                  95

Glu Ile Asp Lys Pro Ser Gln His His His His His His
            100                 105

<210> SEQ ID NO 36
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1241A05

<400> SEQUENCE: 36

Met Gly Val Ser Asp Val Pro Arg Asp Leu Glu Val Val Ala Ala Thr
1               5                   10                  15

Pro Thr Ser Leu Leu Ile Ser Trp Asn His Asn Tyr Ser Tyr Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Gly Val Ala Thr Ala Thr Ile Ser Gly Leu
    50                  55                  60

Lys Pro Gly Val Asp Tyr Thr Ile Thr Val Tyr Ala Val Thr Ser Ser
65                  70                  75                  80

Tyr Lys Tyr Asp Met Gln Tyr Ser Pro Ile Ser Ile Asn Tyr Arg Thr
                85                  90                  95

Glu Ile Asp Lys Pro Ser Gln His His His His His His
            100                 105

<210> SEQ ID NO 37
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1866C02

<400> SEQUENCE: 37

Met Gly Val Ser Asp Val Pro Arg Asp Leu Glu Val Val Ala Ala Thr
1               5                   10                  15

Pro Thr Ser Leu Leu Ile Ser Trp Asp His Asn Tyr Thr Trp Tyr Arg
            20                  25                  30

Tyr Tyr Arg Ile Thr Tyr Gly Glu Thr Gly Gly Asn Ser Pro Val Gln
            35                  40                  45

Glu Phe Thr Val Pro Arg Gly Val Asp Thr Ala Thr Ile Ser Gly Leu
        50                  55                  60

Lys Pro Gly Val Asp Tyr Thr Ile Thr Val Tyr Ala Val Thr Ser Ser
65                  70                  75                  80

Tyr Lys Tyr Asp Ile Gln Tyr Pro Pro Ile Ser Ile Asn Tyr Arg Thr
                85                  90                  95

Glu Ile Asp Lys Pro Ser Gln His His His His His His
            100                 105

<210> SEQ ID NO 38
<211> LENGTH: 109
<212> TYPE: PRT
<213> ORGANISM: Homo sapiens
<220> FEATURE:
<221> NAME/KEY: MISC_FEATURE
<223> OTHER INFORMATION: 1866D11

<400> SEQUENCE: 38

Met Gly Val Ser Asp Val Pro Arg Asp Leu Glu Val Val Ala Ala Thr
1               5                   10                  15

Pro Thr Ser Leu Leu Ile Ser Trp Asp His Asp Tyr Pro Tyr Arg Arg
            20                  25                  30

Tyr Tyr Arg Ile Thr Tyr Gly Glu Thr Gly Gly Asn Ser Pro Val Gln
            35                  40                  45

Glu Phe Thr Val Pro Lys Asp Val Asp Thr Ala Thr Ile Ser Gly Leu
        50                  55                  60

Lys Pro Gly Val Asp Tyr Thr Ile Thr Val Tyr Ala Val Thr Ser Ser
65                  70                  75                  80

Tyr Lys Tyr Asp Ile Gln Tyr Pro Pro Ile Ser Ile Asn Tyr Arg Thr
                85                  90                  95

Glu Ile Asp Lys Pro Ser Gln His His His His His His
            100                 105

<210> SEQ ID NO 39
<211> LENGTH: 109
<212> TYPE: PRT
<213> ORGANISM: Homo sapiens

```
<220> FEATURE:
<221> NAME/KEY: MISC_FEATURE
<223> OTHER INFORMATION: 1866F10

<400> SEQUENCE: 39

Met Gly Val Ser Asp Val Pro Arg Asp Leu Glu Val Val Ala Ala Thr
1               5                   10                  15

Pro Thr Ser Leu Leu Ile Ser Trp Asp His Asp Tyr Pro Tyr Arg Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Asn Ile Asn Thr Ala Thr Ile Ser Gly Leu
    50                  55                  60

Lys Pro Gly Val Asp Tyr Thr Ile Thr Val Tyr Ala Val Thr Ser Thr
65                  70                  75                  80

Leu Lys Tyr Asp Ile Gln Tyr Ser Pro Ile Ser Ile Asn Tyr Arg Thr
                85                  90                  95

Glu Ile Asp Lys Pro Ser Gln His His His His His His
                100                 105

<210> SEQ ID NO 40
<211> LENGTH: 330
<212> TYPE: DNA
<213> ORGANISM: Homo sapiens
<220> FEATURE:
<221> NAME/KEY: misc_feature
<223> OTHER INFORMATION: 1454D02

<400> SEQUENCE: 40
atgggagttt ctgatgtgcc gcgcgacctg gaagtggttg ctgccacccc caccagcctg     60
ctgatcagct gggaccatga ctacccgtac cgtcgatatt accgcatcac ttacggcgaa    120
acaggaggca atagccctgt ccaggagttc actgtgcctc gtaacatcaa cacagctacc    180
atcagcggcc ttaaacctgg cgttgattat accatcactg tgtatgctgt cacttcttct    240
tacaaatacg acatgcagta ctctccaatt tccattaatt accgcacaga aattgacaaa    300
ccatcccagc accatcacca ccaccactga                                     330

<210> SEQ ID NO 41
<211> LENGTH: 330
<212> TYPE: DNA
<213> ORGANISM: Homo sapiens
<220> FEATURE:
<221> NAME/KEY: misc_feature
<223> OTHER INFORMATION: 1454C03

<400> SEQUENCE: 41
atgggagttt ctgatgtgcc gcgcgacctg gaagtggttg ctgccacccc caccagcctg     60
ctgatcagct gggacatgta ctacccgtac tctcgatatt accgcatcac ttacggcgaa    120
acaggaggca atagccctgt ccaggagttc actgtgccta agaatacga cacagctacc    180 atcagcggcc ttaaacctgg cgttgattat accatcactg tgtatgctgt cacttcttct    240
tacaaatacg acatgcagta ctctccaatt tccattaatt accgcacaga aattgacaaa    300
ccatcccagc accatcacca ccaccactga                                     330

<210> SEQ ID NO 42
<211> LENGTH: 330
<212> TYPE: DNA
<213> ORGANISM: Homo sapiens
<220> FEATURE:
```

<221> NAME/KEY: misc_feature
<223> OTHER INFORMATION: 1454B05

<400> SEQUENCE: 42

```
atgggagttt ctgatgtgcc gcgcgacctg gaagtggttg ctgccacccc caccagcctg      60
ctgatcagct ggtaccatga ctacccgtac cgtcgatatt accgcatcac ttacggcgaa     120
acaggaggca atagccctgt ccaggagttc actgtgccta agacgaaga aacagctacc      180 atcagcggcc ttaaacctgg cgttgattat accatcactg tgtatgctgt cacttcttct    240
tacaaatacg acatgcagta ctctccaatt tccattaatt accgcacaga aattgacaaa    300
ccatcccagc accatcacca ccaccactga                                      330
```

<210> SEQ ID NO 43
<211> LENGTH: 330
<212> TYPE: DNA
<213> ORGANISM: Homo sapiens
<220> FEATURE:
<221> NAME/KEY: misc_feature
<223> OTHER INFORMATION: 1454F05

<400> SEQUENCE: 43

```
atgggagttt ctgatgtgcc gcgcgacctg gaagtggttg ctgccacccc caccagcctg      60
ctgatcagct ggtacatgca ttacccgtac tctcgatatt accgcatcac ttacggcgaa     120
acaggaggca atagccctgt ccaggagttc actgtgccta aacagcatga cacagctacc     180
atcagcggcc ttaaacctgg cgttgattat accatcactg tgtatgctgt cacttcttct    240
tacaaatacg acatgcagta ctctccaatt tccattaatt ccgcacaga aattgacaaa     300 ccatcccagc accatcacca ccaccactga                                      330
```

<210> SEQ ID NO 44
<211> LENGTH: 330
<212> TYPE: DNA
<213> ORGANISM: Homo sapiens
<220> FEATURE:
<221> NAME/KEY: misc_feature
<223> OTHER INFORMATION: 1454F07

<400> SEQUENCE: 44

```
atgggagttt ctgatgtgcc gcgcgacctg gaagtggttg ctgccacccc caccagcctg      60
ctgatcagct ggtaccatat gtactcttac cgtcgatatt accgcatcac ttacggcgaa     120
acaggaggca atagccctgt ccaggagttc actgtgcctc gtgacgttga cacagctacc     180
ataagcggcc ttaaacctgg cgttgattat accatcactg tgtatgctgt cacttcttct    240
tacaaatacg acatgcagta ctctccaatt tccattaatt accgcacaga aattgacaaa    300
ccatcccagc accatcacca ccaccactga                                      330
```

<210> SEQ ID NO 45
<211> LENGTH: 330
<212> TYPE: DNA
<213> ORGANISM: Homo sapiens
<220> FEATURE:
<221> NAME/KEY: misc_feature
<223> OTHER INFORMATION: 1454B08

<400> SEQUENCE: 45

```
atgggagttt ctgatgtgcc gcgcgacctg gaagtggttg ctgccacccc caccagcctg      60
ctgatcagct gggaacatga ctacccgtac cgtcgatatt accgcatcac ttacggcgaa     120
acaggaggca atagccctgt ccaggagttc actgtgccta aagacgttga cacagctacc     180
```

```
atcagcggcc ttaaacctgg cgttgattat accatcactg tgtatgctgt cacttcttct    240
tacaaatacg acatgcagta ctctccaatt tccattaatt accgcacaga aattgacaaa    300
ccatcccagc accatcacca ccaccactga                                     330
```

```
<210> SEQ ID NO 46
<211> LENGTH: 330
<212> TYPE: DNA
<213> ORGANISM: Homo sapiens
<220> FEATURE:
<221> NAME/KEY: misc_feature
<223> OTHER INFORMATION: 1454E09

<400> SEQUENCE: 46
atgggagttt ctgatgtgcc gcgcgacctg gaagtggttg ctgccacccc caccagcctg    60
ctgatcagct ggatgcatga ctacccgtac cgtcgatatt accgcatcac ttacggcgaa    120
acaggaggca atagccctgt ccaggagttc actgtgccta tggaagaaga cacagctacc    180
atcagcggcc ttaaacctgg cgttgattat accatcactg tgtatgctgt cacttcttct    240
tacaaatacg acatgcagta ctctccaatt tccattaatt accgcacaga aattgacaaa    300
ccatcccagc accatcacca ccaccactga                                     330
```

```
<210> SEQ ID NO 47
<211> LENGTH: 330
<212> TYPE: DNA
<213> ORGANISM: Homo sapiens
<220> FEATURE:
<221> NAME/KEY: misc_feature
<223> OTHER INFORMATION: 1454F09

<400> SEQUENCE: 47
atgggagttt ctgatgtgcc gcgcgacctg gaagtggttg ctgccacccc caccagcctg    60
ctgatcagct gggaccataa ctactcttac cgtcgatatt accgcatcac ttacggcgaa    120
acaggaggca atagccctgt ccaggagttc actgtgcctc gtcatactga cacagctacc    180
atcagcggcc ttaaacctgg cgttgattat accatcactg tgtatgctgt cacttcttct    240
tacaaatacg acatgcagta ctctccaatt tccattaatt accgcacaga aattgacaaa    300
ccatcccagc accatcacca ccaccactga                                     330
```

```
<210> SEQ ID NO 48
<211> LENGTH: 330
<212> TYPE: DNA
<213> ORGANISM: Homo sapiens
<220> FEATURE:
<221> NAME/KEY: misc_feature
<223> OTHER INFORMATION: 1454H11

<400> SEQUENCE: 48
atgggagttt ctgatgtgcc gcgcgacctg gaagtggttg ctgccacccc caccagcctg    60
ctgatcagct gggaacatga ctacccgtac cgtcgatatt accgcatcac ttacggcgaa    120
acaggaggca atagccctgt ccaggagttc actgtgcctc gtgaagactc tacagctacc    180
atcagcggcc ttaaacctgg cgttgattat accatcactg tgtatgctgt cacttcttct    240
tacaaatacg acatgcagta ctctccaatt tccattaatt accgcacaga aattgacaaa    300
ccatcccagc accatcacca ccaccactga                                     330
```

```
<210> SEQ ID NO 49
<211> LENGTH: 330
```

```
<212> TYPE: DNA
<213> ORGANISM: Homo sapiens
<220> FEATURE:
<221> NAME/KEY: misc_feature
<223> OTHER INFORMATION: 1241A05

<400> SEQUENCE: 49
atgggagttt ctgatgtgcc gcgcgacctg gaagtggttg ctgccacccc caccagcctg      60
ctgatcagct ggaaccataa ctactcttac taccgatatt accgcatcac ttacggcgaa     120
acaggaggca atagccctgt ccaggagttc actgtgcctc gtggagttgc tacagctacc     180
atcagcggcc ttaaacctgg cgttgattat accatcactg tgtatgctgt cacttcttct     240
tacaaatacg acatgcagta ctctccaatt tccattaatt accgcacaga aattgacaaa     300
ccatcccagc accatcacca ccaccactga                                      330

<210> SEQ ID NO 50
<211> LENGTH: 330
<212> TYPE: DNA
<213> ORGANISM: Homo sapiens
<220> FEATURE:
<221> NAME/KEY: misc_feature
<223> OTHER INFORMATION: 1866C02

<400> SEQUENCE: 50
atgggagttt ctgatgtgcc gcgcgacctg gaagtggttg ctgccacccc caccagcctg      60
ctgatcagct gggaccataa ctacacttgg tatcgatatt accgcatcac ttacggcgaa     120
acaggaggca atagccctgt ccaggagttc actgtgcctc gtggagttga tacagctacc     180
atcagcggcc ttaaacctgg cgttgattat accatcactg tgtatgctgt cacttcttct     240
tacaagtacg acattcagta cccgccaatt tccattaatt accgcacaga aattgacaaa     300
ccatcccagc accatcacca ccaccactga                                      330

<210> SEQ ID NO 51
<211> LENGTH: 330
<212> TYPE: DNA
<213> ORGANISM: Homo sapiens
<220> FEATURE:
<221> NAME/KEY: misc_feature
<223> OTHER INFORMATION: 1866D11

<400> SEQUENCE: 51
atgggagttt ctgatgtgcc gcgcgacctg gaagtggttg ctgccacccc caccagcctg      60
ctgatcagct gggaccatga ctacccgtac cgtcgatatt accgcatcac ttacggcgaa     120
acaggaggca atagccctgt ccaggagttc actgtgccta aagacgttga cacagctacc     180
atcagcggcc ttaaacctgg cgttgattat accatcactg tgtatgctgt cacttcgtct     240
tacaaatacg acattcaata cccaccaatt tccattaatt accgcacaga aattgacaaa     300
ccatcccagc accatcacca ccaccactga                                      330

<210> SEQ ID NO 52
<211> LENGTH: 330
<212> TYPE: DNA
<213> ORGANISM: Homo sapiens
<220> FEATURE:
<221> NAME/KEY: misc_feature
<223> OTHER INFORMATION: 1866F10

<400> SEQUENCE: 52
atgggagttt ctgatgtgcc gcgcgacctg gaagtggttg ctgccacccc caccagcctg      60
```

-continued

```
ctgatcagct gggaccatga ctacccgtac cgtcgatatt accgcatcac ttacggcgaa    120
acaggaggca atagccctgt ccaggagttc actgtgcctc gtaacatcaa cacagctacc    180
atcagcggcc ttaaacctgg cgttgattat accatcactg tgtatgctgt cacttcgact    240
ttaaaatacg acattcagta ttctccaatt tccattaatt accgcacaga aattgacaaa    300
ccatcccagc accatcacca ccaccactga                                     330
```

FIBRONECTIN BASED SCAFFOLD DOMAIN PROTEINS THAT BIND IL-23

FIELD OF THE INVENTION

The present invention relates to fibronectin based scaffold domain protein that bind interleukin 23 (IL-23). The invention also relates to the use of the innovative proteins in therapeutic applications to treat autoimmune diseases. The invention further relates to cells comprising such proteins, polynucleotide encoding such proteins or fragments thereof, and to vectors comprising the polynucleotides encoding the innovative proteins.

INTRODUCTION

IL-23 is a member of the IL-12 heterodimeric cytokine family. It contains the p40 subunit, which is shared with IL-12, and a unique p19 subunit. IL-23 signals through a heterodimeric receptor complex consisting of IL-12Rβ1 and IL-23R (Aggarwal, S. et al., "Interleukin-23 promotes a distinct CD4 T cell activation state characterized by the production of interleukin-17", *J. Biol. Chem.*, 278:1910-1914 (2003)). IL-23 is a potential target for the treatment of chronic inflammatory disorders such as multiple sclerosis, rheumatoid arthritis, psoriasis and Crohn's disease.

Fibronectin based scaffolds are a family of proteins capable of evolving to bind any compound of interest. These proteins, which generally make use of a scaffold derived from a fibronectin type III (Fn3) or Fn3-like domain, function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins are Adnectins (Adnexus, a Bristol-Myers Squibb R&D Company).

Fibronectin type III (Fn3) domains comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. Any or all of loops AB, BC, CD, DE, EF and FG may participate in target binding. The BC, DE, and FG loops are both structurally and functionally analogous to the complementarity determining regions (CDRs) from immunoglobulins. U.S. Pat. No. 7,115,396 describes Fn3 domain proteins wherein alterations to the BC, DE, and FG loops result in high affinity TNFα binders. Co-pending U.S. provisional patent application Nos. 61/305,566 and 61/330,706 describe Fn3 domain proteins wherein alterations to the BC, DE, and FG loops result in high affinity IL-23-specific p19 subunit binders. Both provisional applications are herein incorporated by reference.

It would be advantageous to obtain improved fibronectin domain scaffold proteins for therapeutic treatment of autoimmune disorders. A subset of effector T cells that produce interleukin 17 (IL-17; 'Th17 cells') are highly proinflammatory and induce severe autoimmunity. Th17 cells express a distinct subset of cytokines and chemokines compared to Th1 and Th2 cells, including IL-6, tumor necrosis factor (TNF), IL-22, IL-17A and IL-17F as well as the chemokine receptor CCR6. IL-23 promotes the production of IL-17 by activated T cells (Aggarwal, S. et al., "Interleukin-23 promotes a distinct CD4 T cell activation state characterized by the production of interleukin-17", *J. Biol. Chem.*, 278:1910-1914 (2003)) and is a key cytokine to induce expansion of IL-17-producing CD4+ T cells. Exposure to IL-23 seems to be the key feature that determines the pathogenicity of Th17 cells.

SUMMARY OF THE INVENTION

The application provides Adnectins against human IL-23. One aspect of the invention provides for polypeptides comprising Fn3 domain in which one or more of the solvent accessible loops has been randomized or mutated. In some embodiments, the Fn3 domain is an Fn3 domain derived from the wild-type tenth module of the human fibronectin type III domain ($^{10}$Fn3). In some embodiments, the $^{10}$Fn3 polypeptide of the invention is at least 40%, 50%, 60%, 65%, 70%, 75%, 80%, 85%, or 90% identical to the human $^{10}$Fn3 domain In some embodiments, one or more loops selected from BC, DE, and FG may be extended or shortened in length relative to the corresponding human fibronectin loop.

In some embodiments, the polypeptides of the invention comprise a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain.

In some embodiments, the polypeptide of the invention comprises a Fn3 domain that comprises an amino acid sequence at least 80, 85, 90, 95, 98, 99 or 100% identical to the non-loop regions.

In some embodiments, the BC loop of the protein of the invention comprises an amino acid sequence selected from the group consisting of SEQ ID NOs: 2-11.

In some embodiments, the DE loop of the protein of the invention comprises an amino acid sequence selected from the group consisting of SEQ ID NOs: 12-22.

In some embodiments, the FG loop of the protein of the invention comprises an amino acid sequence selected from the group consisting of SEQ ID NOs: 23-25.

In some embodiments, the $^{10}$Fn3 domain may begin and/or end with amino acid substitutions, insertions or deletions.

In some embodiments, the protein of the invention comprises one loop sequence from the BC loop sequences shown in SEQ ID NOs: 2-11, one DE loop sequence shown in SEQ ID NOs: 12-22 and one FG loop sequence shown in SEQ ID NOs: 23-25.

In some embodiments, the protein of the invention comprises a BC, DE and FG loop amino acid sequence at least 70, 75, 80, 85, 90, 95, 98, 99 or 100% identical to of any one of SEQ ID NOS:2-25.

In some embodiments, the anti-IL-23 Adnectin comprises the amino acid sequence of any one of SEQ ID NOS: 27-39.

In some embodiments, the anti-IL-23 Adnectin comprises the Fn3 domain amino acid sequence from position 3-96 of any one of SEQ ID NOS: 27-39.

In one aspect, the anti-IL-23 Adnectin further comprises a pharmacokinetic (PK) moiety. In some embodiments, the PK moiety comprises polyethylene glycol (PEG).

In one aspect, the application provides an anti-IL-23 Adnectin useful in the treatment of autoimmune diseases.

BRIEF DESCRIPTION OF THE FIGURES

FIG. 1a-1b show the full amino acid sequences of the anti-IL23 Adnectin of the invention.

FIGS. 2a-2c show the full nucleic acid sequences of the anti-IL23 Adnectin of the invention.

FIG. 5 shows two orthogonal views of a cartoon diagram of 1454B08 superimposed on $^{10}$Fn3 (PDB 1FNF residues 1416 to 1509). Color code: 1FNF (blue), 1454B08 (cyan). Note the excellent superposition of the core β-strands and the AB and EF loops (at the C-terminal, right-hand side of the molecule). On the left side are the diversified loops: BC, DE and FG. The DE loop, which is quite short, shows little variation in these structures. The BC loop shows modest variation. In contrast, the FG loop shows dramatic variation in position even between the equal-length 1454B08 and $^{10}$Fn3 loops. The N-termini of the $^{10}$Fn3 and that of 1454B08 differs considerably. Figure produced with PyMol (DeLano, 2002).

DETAILED DESCRIPTION OF THE INVENTION

Definitions

Figure 3:
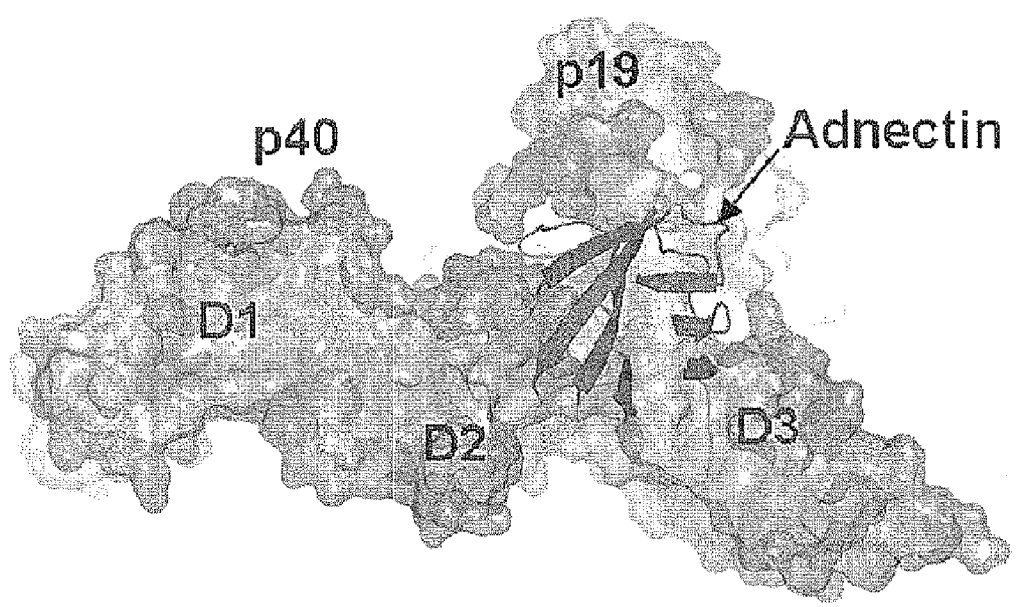
FIG. 3 shows the binding of Adnectin 1454B08 to IL-23. The Adnectin is shown as a cartoon with β-strands colored red, non-repetitive secondary structure colored orange, and diversified loops colored magenta. IL-23 is shown as a surface (gray). This view highlights that Adnectin 1454B08 binds at the interface between the p40 and p19 subunits and that it interacts with both domains D2 and D3 on the p40 subunit. Figure produced with PyMol (DeLano, 2002).

By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or I)). The peptides of the invention are proteins derived from the tenth type III domain of fibronectin that have been modified to bind specifically to IL-23 and are referred to herein as "Adnectin" or "anti-IL-23 Adnectin".

The term "PK" is an acronym for "pharmokinetic" and encompasses properties of a compound including, by way of example, absorption, distribution, metabolism, and elimination by a subject. A "PK modulation protein" or "PK moiety" refers to any protein, peptide, or moiety that affects the pharmokinetic properties of a biologically active molecule when fused to or administered together with the biologically active molecule. Examples of a PK modulation protein or PK moiety include PEG, human serum albumin (HSA) binders (as disclosed in U.S. Publication Nos. 2005/0287153 and 2007/0003549), human serum albumin, Fc or Fc fragments, and sugars (e.g., sialic acid).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR®) software. Those skilled in the art can determine appropriate parameters for measuring alignment, including any algorithms needed to achieve maximal alignment over the full-length of the sequences being compared.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or nonreducing condition using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

Overview

The application provides Adnectins against human IL-23. In order to identify IL-23 specific antagonists, IL-23 was presented to large synthetic libraries of Adnectin using anti-p40 mAbs. Adnectins that bound to IL-23 were screened for binding to human IL-23, competition of the IL-23/IL-23R interaction and inhibition of IL-23 induced signaling in a T-cell line. The anti-IL-23 Adnectins were subjected to further selective pressure by lowering the target concentration and selecting for anti-IL-23 Adnectins with slow off-rates. From this optimization process a family of Adnectin were identified as IL-23 specific inhibitors with favorable biochemical and biophysical properties.

Fibronectin Based Scaffolds

One aspect of the application provides for polypeptides comprising Fn3 domain in which one or more of the solvent accessible loops has been randomized or mutated. In some embodiments, the Fn3 domain is an Fn3 domain derived from the wild-type tenth module of the human fibronectin type III domain ($^{10}$Fn3): VSDVPRDLEVVAATPTSLLI SWDAPAVTVRYYRITYGETGGNSPVQEFTV PGSKSTATISGLKPGVDYTITVYAV TGRGDSPASSKPISINYRT (SEQ ID NO: 1). In the $^{10}$Fn3 sequence above, the BC, DE and FG loops are underlined.

A variety of mutant $^{10}$Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO 02/04523). A variety of additional alterations in the $^{10}$Fn3 scaffold that are either beneficial or neutral have been disclosed. See, for example, Batori et al., *Protein Eng.*, 15(12):1015-1020 (December 2002); Koide et al., *Biochemistry*, 40(34):10326-10333 (Aug. 28, 2001).

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO:1, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87 (Xu et al., *Chemistry & Biology*, 9:933-942 (2002)).

In some embodiments, the $^{10}$Fn3 polypeptide may be at least 40%, 50%, 60%, 65%, 70%, 75%, 80%, 85%, or 90% identical to the human $^{10}$Fn3 domain, shown in SEQ ID NO:1. Much of the variability will generally occur in one or more of the loops. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO:1, provided that such variation does not disrupt the stability of the polypeptide in physiological conditions.

In some embodiments, the disclosure provides polypeptides comprising a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain. In some embodiments, the BC and FG loops are altered, in some embodiments, the BC, DE, and FG loops are altered, i.e., the Fn3 domains comprise non-naturally occurring loops. By "altered" is meant one or more amino acid sequence alterations relative to a template sequence (corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In some embodiments, one or more loops selected from BC, DE, and FG may be extended or shortened in length relative to the corresponding human fibronectin loop. In some embodiments, the length of the loop may be extended by 2-25 amino acids. In some embodiments, the length of the loop may be decreased by 1-11 amino acids. To optimize antigen binding, therefore, the length of a loop of $^{10}$Fn3 may be altered in length as well as in sequence to obtain the greatest possible flexibility and affinity in antigen binding.

In some embodiments, the polypeptide comprises a Fn3 domain that comprises an amino acid sequence at least 80, 85, 90, 95, 98, 99 or 100% identical to the non-loop regions of SEQ ID NO:1, wherein at least one loop selected from BC, DE, and FG is altered. In some embodiments, the altered BC loop has up to 10 amino acid substitutions, up to 4 amino acid deletions, up to 10 amino acid insertions, or a combination thereof. In some embodiments, the altered DE loop has up to 6 amino acid substitutions, up to 4 amino acid deletions, up to 13 amino acid insertions or a combination thereof. In some embodiments, the FG loop has up to 12 amino acid substitutions, up to 11 amino acid deletions, up to 25 amino acid insertions or a combination thereof.

In some embodiments, the BC loop of the protein of the invention comprises an amino acid sequence selected from the group consisting of DHDYPYR (SEQ ID NO: 2), DMYYPYS (SEQ ID NO: 3), YHDYPYR (SEQ ID NO:4), YMHYPYS (SEQ ID NO:5), YHMYSYR (SEQ ID NO:6), EHDYPYR (SEQ ID NO:7), MHDYPYR (SEQ ID NO:8), DHNYSYR (SEQ ID NO:9), NHNYSYY (SEQ ID NO: 10), and DHNYT<u>W</u>Y (SEQ ID NO:11).

In some embodiments, the DE loop of the protein of the invention comprises an amino acid sequence selected from the group consisting of RNIN (SEQ ID NO:12), KEYD (SEQ ID NO:13), KDEE (SEQ ID NO:14), KQHD (SEQ ID NO:15), RDVD (SEQ ID NO:16), KDVD (SEQ ID NO:17), MEED (SEQ ID NO:18), RHTD (SEQ ID NO:19), REDS (SEQ ID NO:20), RGVA (SEQ ID NO:21) and RGVD (SEQ ID NO:22).

In some embodiments, the FG loop of the protein of the invention comprises an amino acid sequence selected from the group consisting of SSYKYDMQYS (SEQ ID NO:23), SSYKYDIQYP (SEQ ID NO:24) and STLKYDIQYS (SEQ ID NO:25).

The $^{10}$Fn3 domain may begin with amino acid alterations. For example, an additional MG sequence may be placed at the N-terminus of an Fn3 domain. The M will usually be cleaved off, leaving a G at the N-terminus. In some embodiments, sequences may be placed at the C-terminus of the $^{10}$Fn3 domain. For example, in site directed PEGylation where a cysteine containing linker such as GSGC (SEQ ID NO: 26) is added to the C-terminus.

In some embodiments, the protein of the invention comprises one loop sequence from the BC loop sequences shown in SEQ ID NOs: 2-11, one DE loop sequence shown in SEQ ID NOs: 12-22 and one FG loop sequence shown in SEQ ID NOs: 23-25. In some embodiments, the protein of the invention comprises a BC, DE and FG loop amino acid sequence at least 70, 75, 80, 85, 90, 95, 98, 99 or 100% identical to of any one of SEQ ID NOS:2-25.

In some embodiments, the anti-IL-23 Adnectin comprises the amino acid sequence of any one of SEQ ID NOS:27-39. In some embodiments, the anti-IL-23 Adnectin comprises the Fn3 domain amino acid sequence from position 3-96 of any one of SEQ ID NOS:27-39. In some embodiments, the anti-IL-23 Adnectin comprises the amino acid sequence at least 70, 75, 80, 85, 90, 95, 98, 99 or 100% identical to any one of SEQ ID NOS:27-39.

In some embodiments, the anti-IL-23 Adnectin comprises the nucleic acid sequence of any one of SEQ ID NOS: 40-52. In some embodiments, the anti-IL-23 Adnectin comprises the nucleic acid sequence at least 70, 75, 80, 85, 90, 95, 98, 99 or 100% identical to any one of SEQ ID NOS: 40-52.

Fibronectin naturally binds certain types of integrins through its integrin-binding motif, "arginine-glycine~aspartic acid" (ROD). In some embodiments, the polypeptide comprises a $^{10}$Fn3 domain that lacks the (RGD) integrin binding motif.

Pharmacokinetic Moieties

In one aspect, the application provides for anti-IL-23 Adnectin further comprising a pharmacokinetic (PK) moiety. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The anti-IL-23 Adnectin may be attached to a moiety that reduces the clearance rate of the polypeptide in a mammal (e.g., mouse, rat, or human) by greater than three-fold relative to the unmodified Adnectin. Other measures of improved pharmacokinetics may include serum half-life, which is often divided into an alpha phase and a beta phase. Either or both phases may be improved significantly by addition of an appropriate moiety.

Moieties that tend to slow clearance of a protein from the blood, herein referred to as "PK moieties", include polyoxyalkylene moieties, e.g., polyethylene glycol, sugars (e.g., sialic acid), and well-tolerated protein moieties (e.g., Fc, Fc fragments, transferrin, or serum albumin). The Adnectin may be fused to albumin or a fragment (portion) or variant of albumin as described in U.S. Publication No. 2007/0048282.

In some embodiments, the PK moiety is a serum albumin binding protein such as those described in U.S. Publication Nos. 2007/0178082 and 2007/0269422.

In some embodiments, the PK moiety is a serum immunoglobulin binding protein such as those described in U.S. Publication No. 2007/0178082.

In some embodiments, the Adnectin comprises polyethylene glycol (PEG). One or more PEG molecules may be attached at different positions on the protein, and such attachment may be achieved by reaction with amines, thiols or other suitable reactive groups. The amine moiety may be, for example, a primary amine found at the N-terminus of a Polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

Pegylation may be achieved by site-directed pegylation, wherein a suitable reactive group is introduced into the protein to create a site where pegylation preferentially occurs. In some embodiments, the protein is modified to introduce a cysteine residue at a desired position, permitting site directed pegylation on the cysteine. PEG may vary widely in molecular weight and may be branched or linear.

In some embodiments, the Adnectin comprises an Fn3 domain and a PK moiety. In some embodiments, the Fn3 domain is a $^{10}$Fn3 domain. In some embodiments, the PK moiety increases the serum half-life of the polypeptide by more than 5, 10, 20, 30, 40, 50, 60, 70, 80, 90, 100, 120, 150, 200, 400, 600, 800, 1000% or more relative to the Fn3 domain alone.

In some embodiments, the PK moiety is a polymeric sugar. In some embodiments, the PK moiety is a polyethylene glycol moiety. In some embodiments the PK moiety is a serum albumin binding protein. In some embodiments the PK moiety is human serum albumin. In some embodiments the PK moiety is a serum immunoglobulin binding protein. In some embodiments, the PK moiety is transferrin. In some embodiments the PK moiety is another Adnectin specific for a serum protein.

Biophysical and Biochemical Characterization

The application provides Adnectin comprising a Fn3 domain that binds to IL-23. As shown in Example 2, polypeptide binding to a target molecule may be assessed in terms of equilibrium constants (e.g., dissociation, $K_D$) and in terms of kinetic constants (e.g., on rate constant, $k_{on}$ and off-rate constant, $k_{off}$), An Adnectin will generally bind to a target molecule with a $K_D$ of less than 500 nM, 100 nM, 10 nM, 1 nM, 500 pM, 200 pM, 100 pM, although higher $K_D$ values may be tolerated where the $k_{off}$ is sufficiently low or the $k_{on}$, is sufficiently high.

The BC, DE and FG loop sequences of the family of anti-IL-23 Adnectin of the invention are presented in Table 1 below, as well as the corresponding full length SEQ ID NO.

TABLE 1

Anti-IL-23 Adnectin Family

| Clone ID | BC Loop | DE Loop | FG loop | SEQ ID NO |
|---|---|---|---|---|
| 1454D02 | DHDYPYR | RNIN | SSYKYDMQYS | 27 |
| 1454C03 | DMYYPYS | KEYD | SSYKYDMQYS | 28 |
| 1454B05 | YHDYPYR | KDEE | SSYKYDMQYS | 29 |
| 1454F05 | YMHYPYS | KQHD | SSYKYDMQYS | 30 |
| 1454F07 | YHMYSYR | RDVD | SSYKYDMQYS | 31 |
| 1454B08 | EHDYPYR | KDVD | SSYKYDMQYS | 32 |
| 1454E09 | MHDYPYR | MEED | SSYKYDMQYS | 33 |
| 1454F09 | DHNYSYR | RHTD | SSYKYDMQYS | 34 |
| 1454H11 | EHDYPYR | REDS | SSYKYDMQYS | 35 |
| 1241A05 | NHNYSYY | RGVA | SSYKYDMQYS | 36 |
| 1866C02 | DHNYTWY | RGVD | SSYKYDIQYP | 37 |
| 1866D11 | DHDYPYR | KDVD | SSYKYDIQYP | 38 |
| 1866F10 | DHDYPYR | RNIN | STLKYDIQYS | 39 |

Nucleic Acid-protein Fusion Technology

In one aspect, the application provides Adnectins comprising fibronectin type III domains that bind IL-23. One way to rapidly make and test Fn3 domains with specific binding properties is the nucleic acid-protein fusion technology of Adnexus, a Bristol-Myers Squibb R&D Company. This disclosure utilizes the in vitro expression and tagging technology, termed PROfusion, which exploits nucleic acid-protein fusions (RNA- and DNA-protein fusions) to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558, 6,261,804, 6,214,553, 6,281,344, 6,207,446, 6,518,018, 6,818,418; and Roberts et al., *Proc Natl. Acad. Sci.*, 94:12297-12302 (1997), herein incorporated by reference.

Vectors and Polynucleotides Embodiments

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*, 100(2):438-442 (Jan. 21, 2003); Sinclair et al., *Protein Expr. Purif.*, 26(1):96-105 (October 2002); Connell, N. D., *Curr. Opin. Biotechnol.*, 12(5):446-449 (October 2001); Makrides et al., *Microbial. Rev.*, 60(3):512-538 (September 1996); and Sharp et al., *Yeast*, 7(7):657-678 (October 1991).

General techniques for nucleic acid manipulation are described for example in Sambrook et al., *Molecular Cloning: A Laboratory Manual*, 2nd Edition, Vols. 1-3, Cold Spring Harbor Laboratory Press (1989) or Ausubel, F. et al., *Current Protocols in Molecular Biology*, Green Publishing and Wiley-Interscience, New York (1987)) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene, to facilitate recognition of transformants, are additionally incorporated.

The proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell.

For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders.

For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein of the invention, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein of the invention. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tall to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding proteins of the invention by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also, Yaniv, *Nature*, 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein of the invention. One useful transcription termination component is the bovine growth hormone polyadenylation region. See WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, Elsevier, New York (1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the Saccharomyces genus, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (*Biotechnology*, 6:47 (1988)). Examples of suitable mammalian host cell lines include endothelial cells, CO8-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* the preferred method for expression. The protein is then purified from culture media or cell extracts.

Protein Production

Host cells are transformed with the herein-described expression or cloning vectors for protein production and cultured in conventional nutrient media modified as appropriate for inducing promoters, selecting transformants, or amplifying the genes encoding the desired sequences. In the examples shown here, the host cells used for high-throughput protein production (HTPP) and mid-scale production was the BL21(DE3) plysS bacterial strain. The culture conditions, such as temperature, pH, and the like, are those previously used with the host cell selected for expression, and will be apparent to the ordinarily skilled artisan.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Proteins of the invention can also be produced by chemical synthesis (e.g., by the methods described in *Solid Phase Peptide Synthesis,* 2nd Edition, The Pierce Chemical Co, Rockford, Ill. (1984)). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, or preferably at least 95% pure, and most preferably at least 99% pure. Regardless of the exact numerical value of the purity, the polypeptide is sufficiently pure for use as a pharmaceutical product.

Therapeutic in Vivo Uses

In one aspect, the application provides anti-IL-23 Adnectin useful in the treatment of autoimmune diseases such as lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g., insulin dependent diabetes mellitus, type I diabetes mellitus), Good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjögren's syndrome, rheumatic diseases (e.g., rheumatoid arthritis), polymyositis, scleroderma, and mixed connective tissue disease. The application also provides methods for administering anti-IL-23 Adnectin to a subject. In some embodiments, the subject is a human. In some embodiments, the anti-IL-23 Adnectins are pharmaceutically acceptable to a mammal, in particular a human. A "pharmaceutically acceptable" polypeptide refers to a polypeptide that is administered to an animal without significant adverse medical consequences, such as essentially endotoxin free or having very low endotoxin levels.

Formulation and Administration

The application further provides pharmaceutically acceptable compositions comprising the anti-IL-23 Adnectin described herein, wherein the composition is essentially endotoxin free. Therapeutic formulations comprising anti-IL-23 Adnectin are prepared for storage by mixing the described Adnectin having the desired degree of purity with optional physiologically acceptable carriers, excipients or stabilizers (Osol, A., ed., *Remington's Pharmaceutical Sciences,* 16th Edition (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethoninm chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, PLURONIC® or polyethylene glycol (PEG).

The formulations herein may also contain more than one active compound as necessary for the particular indication being treated, preferably those with complementary activities that do not adversely affect each other. Such molecules are suitably present in combination in amounts that are effective for the purpose intended.

The formulations to be used for in vivo administration must be sterile. This is readily accomplished by filtration through sterile filtration membranes The skilled artisan will understand that the dosage of each therapeutic agent will be dependent on the identity of the agent.

For therapeutic applications, the anti-IL-23 Adnectin is administered to a subject, in a pharmaceutically acceptable dosage form. They can be administered intravenously as a bolus or by continuous infusion over a period of time, or by subcutaneous routes. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, (2) 0.9% saline (0.9% w/v NaCl), and (3) 5% (w/v) dextrose.

The method of the present invention can be practiced in vitro, in vivo, or ex vivo.

Administration of anti-IL-23 Adnectin, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being administered.

When present in an aqueous dosage form, rather than being lyophilized, the protein typically will be formulated at a concentration of about 0.1 mg/ml to 100 mg/ml, although wide variation outside of these ranges is permitted. For the treatment of disease, the appropriate dosage of anti-IL-23 Adnectin will depend on the type of disease to be treated, the severity and course of the disease, whether the Adnectin is administered for preventive or therapeutic purposes, the course of previous therapy, the patient's clinical history and response to the Adnectin, and the discretion of the attending physician. The protein is suitably administered to the patient at one time or over a series of treatments.

Structure of Anti-IL-23 Adnectin/IL-23 Protein Complex

Analysis of the structure of IL-23-binding Adnectins yields multiple insights into the molecular interactions between this Adnectin and its target. Given that target binding is mediated by a set of Adnectin loop residues that were mutated from the wild-type sequence, it is not surprising that many of these residues are observed to contact the target. It is more interesting to note that not all the residues in the BC, DE, and FG loops that were diversified in the library and selected as non-wild-type residues are found to be at or near the Adnectin/target interface. Conversely, several wild-type residues outside of the diversified loops (BC, DE, VG) interact with the target protein. Comparing main chain conformation of the target-binding Adnectin to wild-type $^{10}$Fn3, differences were observed from the wild type in each of the three diversified loops and the N-terminus may undergo conformational changes to bind to the target protein's surface.

As described in Example 3, the following residues from the Adnectin are found to contact IL-23: N-terminal region: Pro5, Arg 6, Asp 7, BC-loop: Glu 23, His 24, Asp 25, Tyr 26, Pro 27, Tyr 28, Arg 30, C-strand: Tyr 31; CD-loop: Gly 40, Asn 42, Val 45; F-strand: Tyr 73, Val 75; PG-loop: Thr 76, Ser 77, Ser 78, Tyr 79, Lys 80, Tyr 81, Asp 82, Met 83, Gin 84, Tyr 85, Ser 86, Pro 87. Note that these contacting residues include a large number of non-diversified residues.

In particular, Tyr 26, Tyr 28, Asp 82 and Tyr 85 were completely conserved in this set of adnectins showing that these amino acids are critical, and substitutions of these amino acids with any of the other 19 natural amino acids is likely to drastically reduce or eliminate binding to IL-23. The consensus sequences include Tyr 26 and Tyr 28 in the BC loop and Ser 77, Lys 80, Tyr 81, Asp 82, Gln 84 and Tyr 85 of the FG loop. The combination of these amino acids is likely to play an important role in the high affinity binding of 1454B08 to IL-23, although clones with one or two mutations in these positions may retain some binding.

It should be noted that the N-terminus is flexible in Adnectins. In $^{10}$Fn3, the position is dictated by the link to $^9$Fn3. The crystal structure described in Example 3 shows that the N-terminus of 1454B08 is folded away compared to $^{10}$Fn3 N-termini presumably to avoid collision with IL-23 and that Pro5, Arg6, Asp7 in the N-terminal region prior to the A strand are in contact with the target.

By the combination of energetics calculations described in Example 3 and alanine mutagenesis, a minimal energetic paratope for 1454B08 has been identified as consisting of at least Tyr 28 from the BC loop, Tyr 81 from the FG loop, and Pro 87, a non-diversified residue, from the C-terminal end of the FG loop.

The structure of IL-23 complex with Adnectin shows that residues that interact with the target protein may extend far outside of the diversified loops of the Adnectins. Clearly, the importance of residues outside the binding loops has been demonstrated by interaction energy calculations and targeted mutagenesis experiments which show the ability to increase or decrease binding affinity. Mutagenesis of several contact residues to alanine shows the importance of hydrophobic interactions to intermolecular interactions.

In addition to the ability of residues outside of the diversified loops to interact with the target, this structure shows several other features. The IL-23/1454B08 structure shows that despite the large number of residues involved in the interaction, not all residues in the three diversified loops on the Adnectin were in direct contact with IL-23. Moreover, the loops and N-terminus may adopt conformations other than that seen in the wild-type $^{10}$Fn3 structure, Presumably, the loops are somewhat flexible, but only certain conformations are capable of productively interacting with a target, which is what is seen in the complexes. Adnectins, by virtue of their small size and convex shape, may enable binding to surfaces that are inaccessible to antibodies, for example, the concave junction between the p40 and p19 domains of IL-23. Finally, although Adnectins are less than half the size of antibody Fv domain dimers, they are fully capable of burying as much surface with theft targets. All of these capabilities suggest Adnectins may prove a very successful platform for developing protein therapeutics.

Description and Location of the Structure Coordinates Table

The structure coordinates of the crystal structure of IL-23 in complex with an adnectin were deposited on Feb. 29, 2011 with the RCSB Protein Data Bank (www.pdb.org, Berman, H. M. et al., "The Protein Data Bank", *Nucleic Acids Research*, 28: 235-242 (2000) and www.wwpdb.org, Berman, H. M. et al., "Announcing the worldwide Protein Data Bank", *Nature Structural Biology*, 10(12):98 (2003)), and has been accorded PDB ID: 3QWR.

EXAMPLES

Example 1

Material and Methods Used Herein

High Throughput Protein Production (HTPP)

Selected binder cloned into pET9d vector and transformed into *E. coli* BL21 DE3 plysS cells were inoculated in 5 ml LB medium containing 50 μg/mL kanamycin in a 24-well format and grown at 37° C. overnight. Fresh 5 ml LB medium (50 μg/mL kanamycin) cultures were prepared for inducible expression by aspiration 200 μl from the overnight culture and dispensing it into the appropriate well. The cultures were grown at 37° C. until $A_{600}$ 0.6-0.9. After induction with 1 mM isopropyl-β-thiogalactoside (IPTG) the culture was grown for 6 hours at 30° C. and harvested by centrifugation for 10 minutes at 2750 g at 4° C.

Cell pellets (in 24-well format) were lysed by resuspension in 450 μl of Lysis buffer (50 mM $NaH_2PO_4$, 0.5 M NaCl, 1× Complete Protease Inhibitor Cocktail-EDTA free (Roche), 1 mM PMSF, 10 mM CHAPS, 40 mM Imidazole, 1 mg/ml lysozyme, 30 μg/ml DNAse, 2 μg/ml aprotonin, pH 8.0) and shaken at room temperature for 1-3 hours. Lysates were clarified and re-racked into a 96-well format by transfer into a 97-well Whatman GF/D UNIFILTER® fitted with a 96-well, 1.2 ml catch plate and filtered by positive pressure. The clarified lysates were transferred to a 96-well Ni-Chelating Plate that had been equilibrated with equilibration buffer (50 mM $NaH_2PO_4$, 0.5 M NaCl, 40 mM Imidazole, pH 8.0) and was incubated for 5 min. Unbound material was removed by vacuum. The resin was washed 2×0.3 ml/well with Wash buffer #1 (50 mM $NaH_2PO_4$, 0.5 M NaCl, 5 mM CHAPS, 40 mM Imidazole, pH 8.0) with each wash removed by vacuum. Prior to elution each well was washed with 50 μl Elution buffer (PBS+20 mM EDTA), incubated for 5 min and this wash was discarded by vacuum. Protein was eluted by applying an additional 100 μl of Elution buffer to each well. After a 30 minute incubation at room temperature the plate(s) were centrifuged for 5 minutes at 200 g and eluted protein is collected in 96-well catch plates containing 5 μl of 0.5M $MgCl_2$ added to the bottom of elution catch plate prior to elution. Eluted protein was quantified using a BCA assay with SGE as the protein standard.

Midscale Expression and Purification of Insoluble Fibronectin-based Scaffold Protein Binders For expression, selected clone(s), followed by the HIS6tag, were cloned into a pET9d vector and were expressed in *E. coli* BL21 DE3 plysS cells. Twenty ml of an inoculum culture (generated from a single plated colony) was used to inoculate 1 liter of LB medium or TB-Overnight Expression Media (auto induction) containing 50 μg/ml Kanamycin and 34 μg.ml chloramphenicol. Cultures in LB medium were incubated at 37° C. until A600 0.6-1.0 at which time they were induced with 1 mM isopropyl-β-thiogalactoside (IPTG) and grown for 4 hours at 30° C. Cultures grown in TB-Overnight Expression Media were incubated at 37° C. for 5 hours at which time the temperature was lowered to 18° C. grown for 19 hours. Cultures were harvested by centrifugation for 30 minutes at ≥10,000 g at 4° C. Cell pellets were frozen at −80° C. the cell pellet was resuspended in 25 ml of lysis buffer (20 mM $NaH_2PO_4$, 0.5 M NaCl, 1× Complete Protease. Inhibitor Cocktail-EDTA free (Roche), pH 7.4) using an ULTRA-TURRAX® homogenizer (IKA works) on ice. Cell lysis was achieved by high pressure homongenization (≥18,000 psi) using a Model M-110S MICROFLUIDIZER® (Microfluidics). The insoluble fraction was separated by centrifugation for 30 minutes at ≥23,300 g at 4° C. The insoluble pellet recovered from centrifugation of the lysate was washed with 20 mM sodium phosphate, 500 mM NaCl, pH 7.4. The pellet was resolubilized in 6.0M guanidine hydrochloride in 20 mM sodium phosphate, 500 mM NaCl pH 7.4 with sonication followed by incubation at 37 degrees for 1-2 hours. The resolubilized pellet was filtered to 0.45 μm and loaded onto a HISTRAP® column equilibrated with the 20 mM sodium phosphate, 500 mM NaCl, 6.0 M guanidine pH7.4 buffer. After loading, the column was washed for an additional 25 CV with the same buffer. Bound protein was eluted with 50 mM Imidazole in 20 mM sodium phosphate, 500 mM NaCl, 6.0M guanidine-HCl pH7.4. The purified protein was refolded by dialysis against 50 mM sodium acetate, 150 mM NaCl pH 4.5 or PBS pH 7.2.

Midscale Expression and Purification of Soluble Fibronectin-base Scaffold Protein Binders As an alternative to purification of insoluble binders, the purification of soluble binders may also be used. For expression, selected clone(s), followed by the HIS6tag, were cloned into a pET9d vector and were expressed in *E. coli* BL21 (DE3) plysS cells. Twenty ml of an inoculum culture (generated from a single plated colony) was used to inoculate 1 liter of LB medium or TB-Overnight Expression Media (auto induction) containing 50 μg/ml Kanamycin and 34 μg/ml chloramphenicol. Cultures in LB medium were incubated at 37° C. until A600 0.6-1.0 at which time they were then induced with 1 mM isopropyl-β-thiogalactoside (IPTG) and grown for 4 hours at 30° C. Cultures grown in TB-Overnight Expression Media were incubated at 37° C. for 5 hours at which time the temperature was lowered to 18° C. grown for 19 hours. Cultures were harvested by centrifugation for 30 minutes at ≥10,000 g at 4° C. Cell pellets are frozen at −80° C. The cell pellet is resuspended in 25 ml of lysis buffer (20 mM $NaH_2PO_4$, 0.5 M NaCl, 1× Complete Protease Inhibitor Cocktail-EDTA free (Roche), pH 7.4) using an ULTRA-TURRAX® homogenizer (IKA works) on ice. Cell lysis is achieved by high pressure homongenization (≥18,000 psi) using a Model M-110S MICROFLUIDIZER® (Microfluidics). The soluble fraction is separated by centrifugation for 30 minutes at 23,300 g at 4° C. The supernatant is clarified via 0.45 μm filter. The clarified lysate is loaded onto a HIS-TRAP® column (GE) pre-equilibrated with the 20 mM sodium phosphate, 500M NaCl pH 7.4. The column is then washed with 25 column volumes of the same buffer, followed by 20 column volumes of 20 mM sodium phosphate, 500 mM NaCl, 25 mM Imidazole, pH 7.4 and then 35 column volumes of 20 mM sodium phosphate, 500 mM NaCl, 40 mM Imidazole, pH 7.4. Protein is eluted with 15 column volumes of 20 mM sodium phosphate, 500 M NaCl, 500 mM Imidazole, pH 7.4, fractions are pooled based on absorbance at A280 and are dialyzed against 1× PBS, 50 mM Tris, 150 mM NaCl, pH 8.5 or 50 mM NaOAc, 150 mM NaCl, pH4.5. Any precipitate is removed by filtering at 0.22 μm.

Example 2

In Vitro Characterization

Determination of Binding Constants

The anti-His antibody, mAb050 (RnD Systems, MN) was diluted to 20 μg/mL in acetate, pH 5.0 and immobilized to ~9000 RU on flow cells 1 and 2 of a CM5 chip surface (GE Healthcare, Piscataway, N.J.) according to the manufacturer's instructions. All surface plasmon experiments were conducted in HBS-EP (10 mM Hepes 150 mM NaCl 3 mM EDTA 0.05% Surfactant P20) at 25° C. IL-23 was injected over anti-His mAb captured Adnectins for 2 minutes followed by a 10 minute dissociation phase. Kinetic parameters were calculated using the T100. Biaevaluation.

TABLE 2

Binding Constants

| Clone ID | On-rate ($k_a$, $M^{-1}s^{-1}$) | Off-rate ($k_d$, $s^{-1}$) | Affinity ($K_D$, M) |
|---|---|---|---|
| 1454D02 | 4.57E+04 | 4.38E−04 | 9.57E−09 |
| 1454C03 | 1.20E+05 | 4.68E−04 | 3.91E−09 |
| 1454B05 | 2.98E+05 | 6.77E−04 | 2.27E−09 |
| 1454F05 | 1.11E+05 | 5.25E−04 | 4.75E−09 |
| 1454F07 | 4.74E+04 | 4.47E−04 | 9.43E−09 |
| 1454B08 | 1.10E+05 | 4.09E−04 | 3.72E−09 |
| 1454E09 | 5.66E+04 | 5.69E−04 | 1.01E−08 |
| 1454F09 | 1.25E+05 | 9.28E−04 | 7.45E−09 |
| 1454H11 | 8.10E+04 | 2.27E−04 | 2.80E−09 |
| 1241A05 | 7.28E+03 | 2.36E−04 | 3.26E−08 |

STAT3 Phosphorylation on Kit225 Cells

Parham et al. ("A receptor for the heterodimeric cytokine IL-23 is composed of IL-12Rbeta1 and a novel cytokine receptor subunit, IL-23R", *J. Immunol.*, 168(11):5699-5708 (Jun. 1, 2002)) cloned the IL-23R from the human IL-2 dependent T-cell line, Kit225. These cells have been characterized for expression of both IL-12RB1 and IL-23R by FACS analysis and respond to IL-23 by stimulation of pSTAT3 and to IL-12 by stimulation of pSTAT4. Kit225 cells were seeded into 96-well plates and quiesced in the absence of FBS and IL-2 for 3 hrs at 37° C. Following this incubation, human recombinant IL-23 (or IL-23 preincubated with antagonist for 1 hr) was applied and the cells returned to the incubator for 15 minutes at 37° C. to stimulate the phosphorylation of STAT3 (abbreviated as p-STAT3). Each condition was assayed in duplicate in 96-well plates. Stimulation was stopped by placing the cells on ice and addition of ice-cold PBS. Finally, the cells were pelleted and lysed following standard protocols and pSTAT3 production detected by ELISA.

Inhibition of the IL-23 induced pSTAT3 was demonstrated by a titration of anti-p19 polyclonal antibody (AF1716). Clone 1241A05 had similar activity to the anti-p19 polyclonal antibody with an $IC_{50}$ of ~31 nM. (Table 3)

TABLE 3

Inhibition of IL-23 Induced STAT3 Phosphorylation by Anti-IL-23 Antagonists

| | pSTAT3 $IC_{50}$ (nM) |
|---|---|
| 1866F10 | 0.06 |
| 1866C02 | 0.03 |
| 1866D11 | 0.03 |
| 1454B08 | 0.3 |
| 1454C03 | 0.44 |
| 1454D02 | 0.48 |
| 1454H11 | 0.45 |
| 1241A05 | 30.7 |
| anti-p19 (AF1716) | 36.5 |

Example 3

Structure of Anti-IL-23 Adnectin/Protein Complex

Expression and Purification of Anti-IL-23 Adnectin for Co-crystallization Studies Adnectins were expressed by transforming competent BL21 (DE3) cells (Calbiochem) with the genes encoding the Adnectin cloned into vector pET9d (New England Biolabs, Ipswich, Mass.). Transformants were grown with aeration in auto-induction media (EMD Biosciences), supplemented with kanamycin, for six hours at 37° C. followed by eighteen hours at 20° C. The cells were harvested by centrifugation and frozen at −80° C.

Frozen cells were thawed and resuspended in 50 mM Sodium phosphate, 300 mM Sodium chloride, 10 mM Imidazole, pH 7.5. Once solubilized, DNAse (20 ng/µL) was added to the mixture. The cells were mechanically lysed (Avestin Emulsiflex—C3), centrifuged, and the supernatant was loaded onto an IMAC column (Qiagen, Ni-NTA, 30 mL). The Adnectin was eluted using an Imidazole step gradient (washed with 50 mM Sodium phosphate, 300 mM Sodium chloride, 30 mM Imidazole, pH 7.5 and eluted with 50 mM Sodium phosphate, 300 mM Sodium chloride, 400 mM Imidazole, pH 7.5). The elution pool was dialyzed into phosphate-buffered saline (PBS), pH 7.4.

1454B08 bound immobilized IL-23 with a $K_D$ of 3.7 nM and competed with the IL-23/IL-23R interaction with an $IC_{50}$ of 1 nM in a biochemical competition assay.

Preparation of Adnectin Affinity Column

CNBr-activated SEPHAROSE® 4 Fast Flow resin (GE Cat #17-0987-01) was prepared according to the published instructions (GE Healthcare 71-5000-15 AD). The Adnectin was incubated with the resin overnight, at 4° C., with shaking. Coupling efficiency was >98% (determined by A280).

Expression/Purification of Human IL-23

Human IL-23 was expressed in Sf9 cells by employing a bi-cistronic construct for the p40 and p19 subunits. The media containing secreted IL-23 was concentrated and buffer exchanged into either PBS or TBS by tangential flow filtration. The concentrate was loaded onto the Adnectin affinity column at a flow rate of 20 cm/hr (different size columns were used for different preparations). The column was washed for five column volumes with the TFF buffer, followed by a step elution with 0.1 M Acetate, pH 4.0, 1.0 M NaCl. The eluate was neutralized with Tris HCl, pH 8.0 (1/10 volume; the final Tris concentration was 0.1M), pooled, and concentrated. The sample was further purified and buffer exchanged into HBS on a prep scale SUPERDEX®200 size exclusion chromatography (SEC) column.

Preparation of IL-23/1454B08 Complex

Human IL-23 and Adnectin were mixed at 1:3 molar ratio incubated overnight at 4° C. The 1:1 complex was isolated by size exclusion chromatography on a SUPERDEX® 200 column (GE Healthcare) in a running buffer containing 25 mM HEPES, pH 7.0, 200 mM NaCl. To ensure that no free IL-23 was present, a one-fold molar excess of the free Adnectin, which was separated on the column, was added to the complex. The final complex was concentrated to 12 mg/mL.

Crystallization of IL-23/1454B08 Complex

The Human IL-23/1454B08 complex was crystallized at 20° C. using sitting drop vapor diffusion method by mixing 1 µL of protein complex with 1 µL of reservoir solution containing 1M tri-sodium citrate, 0.2M sodium chloride, 0.1 M Tris, pH 7.0. Crystal quality was improved by seeding.

Data Collection and Processing

Data for IL-23/1454B08 complex was collected at beamline 17ID at IMCACAT at the Advanced Photon Source at Argonne National Laboratory. The wavelength used was 1.0 Å and the detector was a MAR 165 CCD at a distance of 200 mm. Rotation images of 0.5° were collected for 3 seconds each for a sweep of 150°. Data were indexed, integrated, and scaled with d*TREK (Pflugrath, "The finer things in X-ray diffraction data collection", *Acta Crystallogr. Sect. D,* 55:1718-1725 (1999)). Space group, unit cell parameters and data collection statistics are listed in Table 4 below.

TABLE 4

Data Collection Statistics

| Shell | Resolution Range (Å) IL-23/1454B08 complex | Measured | Unique | Redundancy $I2_12_12_1$; a = 77.7 Å; b = 91.7 Å; c = 225.8 Å | % Complete | R-value | $I/\sigma_I$ |
|---|---|---|---|---|---|---|---|
| First | 42.47-6.99 | 5078 | 1313 | 3.9 | 93.3 | 0.057 | 16.4 |
| Last | 3.37-3.25 | 5027 | 1287 | 3.9 | 99.5 | 0.320 | 3.2 |
| Overall | 42.47-3.25 | 51111 | 12835 | 4.0 | 98.0 | 0.096 | 7.6 |

Molecular Replacement

A model for the Adnectins was derived from PDB 1FNF using residues 1416-1437, 1444-1466, 1470-191, and 1502-1509, i.e., deleting the BC, EF, and FG loops. The model for IL-23 was a structure determined at BMS in a different crystal form (V. Ramamurthy and S. Sheriff, unpublished) from those published in the literature (3DUH, 3D87). PHASER (McCoy et al., "Phaser crystallographic software", *J. Appl. Crystallogr.,* 40:658-674 (2007)) was used for molecular replacement paying attention to the translation function Z-scores and the Log Likelihood Gain as each piece was added. When PHASER failed to find the Adnectin in the IL-23/1454B08 complex, a six-dimensional search using the AMoRe translation function was successfully used (Sheriff et al., "Implementation of a six-dimensional search using the AMoRe translation function for difficult molecular-replacement problems", *J. Appl. Crystallogr.* 32:98-101 (1999); Navaza, "AMoRe: an automated package for molecular replacement", *Acta Crystallgr. Sect. A,* 50:157-163 (1994); Navaza et al., "On the fast translation functions for molecular replacement", *Acta Crystallgr. Sect. A,* 51:445-449 (1995); CCP4, "The CCP4 Suite: programs for protein crystallography", *Acta Cryst.,* D50:760-763 (1994)).

Model Building, Refinement and Display Graphics

COOT (Emsley et al., 2004 Coot: model-building tools for molecular graphics. *Acta Crystallogr. Sect. D,* 60:2126-2132 (2004); Emsley et al., "Features and Development of COOT", *Acta Crystallogr. Sect. D,* 66:486-501 (2010)) was used for model building and general observation of the structure. Refinement was carried out with autoBUSTER from Global-Phasing, Ltd. (Bricogne et al., 2009 BUSTER, version 2.8.0. Cambridge, United Kingdom: Global Phasing Ltd.). Display graphics were produced with PyMOL (DeLano, 2002, The PyMol Molecular Graphics System (2002). DeLano Scientific, San Carlos, Calif., US. http:/www.pymol.org). Refinement statistics are listed in Table 5 below.

TABLE 5

Refinement Statistics

| | IL-23/1454B08 complex |
|---|---|
| R-work | 0.216 |
| R-free | 0.261 |
| Number of protein atoms | 3990 |
| Number of carbohydrate atoms | 50 |
| Number of solvent atoms | 1 |
| r.m.s. bond distances, Å | 0.010 |
| r.m.s. angle distances, ° | 1.3 |

Buried surface area was calculated with the program MS (Connolly, "Analytical Molecular Surface Calculation", *J. Appl. Crystallogr.,* 16:548-558 (1983)) using a 1.7 Å probe sphere extended atomic radii as defined by Gelin et al., "Side-chain torsional potentials: effect of dipeptide, protein and solvent environment", *Biochemistry,* 18:1256-1268 (1979)). Contacting residues were as defined by Sheriff et al., "Structure of Myohemerythrin in the Azidomet State at 1.7/1.3 Å Resolution", *J. Mol. Biol.,* 197:273-296 (1987) and Sheriff, "Some methods for examining the interactions between two molecules", *Immunomethods,* 3:191-196 (1993), which used extended atomic radii as defined by Gelin et al. (1979).

Estimates of Residue Free Energies and Interaction Energies

The protein complex was optimized using the Protein Preparation WIZARD® workflow in MAESTRO 9.0.211 (Schrodinger, LLC. 2009). During this process side chain protonation states, histidine tautomers and terminal Chi rotamers for histidine, asparagine and glutamine side chains are optimized. The final step in the workflow is restrained minimization of the complex (0.3 Å RMSD) which allows for subtle optimization of the complex within the OPLS_2005 force field. Protein models were created for each mutant protein using PRIME side chain refinement protocol followed by two minimization steps. The first minimization was applied to only side chains for the subset of residues that were within 5 Å of a mutation site. The final minimization step was applied to the same subset of residues but it included the backbone of the residues in the minimization.

The estimate of Gibbs free energy was calculated as described previously (Novotny et al., "On the attribution of binding energy in antigen-antibody complexes McPC 603, D1.3, and HyHel-5", *Biochemistry,* 28:4735-4749 (1989); Krystek et al., "Affinity and specificity of serine endopeptidase-protein inhibitor interactions", *J. Mol. Biol.,* 234:661-679 (1993)) and implemented in a python script using MAESTRO (Maestro, version 9.0, Schrodinger, LLC, New York, N.Y., 2009). The residue interaction energies were determined using the OPLS_2005 force field as implemented in the Component Interactions script (Schrodinger, LLC) using Macromodel (MacroModel, version 9.7, Schrodinger, LLC, New York, N.Y., 2009). The script calculates the molecular mechanics interaction energy between a set of residues and outputs the individual VDW and electrostatic contribution terms. For the electrostatic component, distance-dependent dielectric was used with a constant of 4.0, similar to the free energy calculations.

Overview of the Structure of the IL-23/1454B08 Complex

IL-23 is a two subunit protein consisting of a p40 subunit that is shared with IL-12 and a p19 subunit that is distinct from the p35 subunit of IL-12. The p40 subunit consists of three Ig-like 7-stranded β-sheet domains, while the p19 consists of a 4-helix bundle. 1454B08 binds at the junction of the p40 and p19 subunits making considerable interactions with both (FIG. 3) including domains 2 and 3 of the p40 subunit. Moreover, although the three diversified loops (BC, DE, and FG) are towards the center of the interface, interactions extend along the β-strands away from the BC, DE, and FG loop end, and interactions are observed even with the CD loop on the opposite end of the molecule. This concave site is likely inaccessible to antibody combining sites which are much larger, consisting of two domains from separate subunits and six hypervariable loops. In fact, the Adnectin binding site is dramatically different from that of the one known antibody complex for IL-23 (PDB 3D85), which binds only to the p19 subunit (Beyer et al., "Crystal Structures of the Pro-inflammatory Cytokine Interleukin-23 and its Complex with a High-affinity Neutralizing Antibody", *J. Mol. Biol.*, 382:942-955 (2008)).

Specific Interactions of Adnectin 1454B08 with IL-23

The interaction between the Adnectin and IL-23 is quite large, burying ~1320 Å$^2$ on the Adnectin surface and ~1390 Å$^2$ on the IL-23 surface. This amount of buried surface area is larger than most antibody/antigen interactions and, presumably, reflects the concave nature of the binding site on IL-23. Despite the large interacting surface, the affinity of 1454B08 for IL-23 is the same order of magnitude as the antibodies for their protein antigens. The Sc statistic for this complex is 0.73, which suggests that it is more complementary than the antibody/antigen complexes surveyed by Lawrence et al. ("Shape Complementarity at Protein/Protein Interfaces", *J. Mol. Biol.*, 234:946-950 (1993)).

Figure 4:
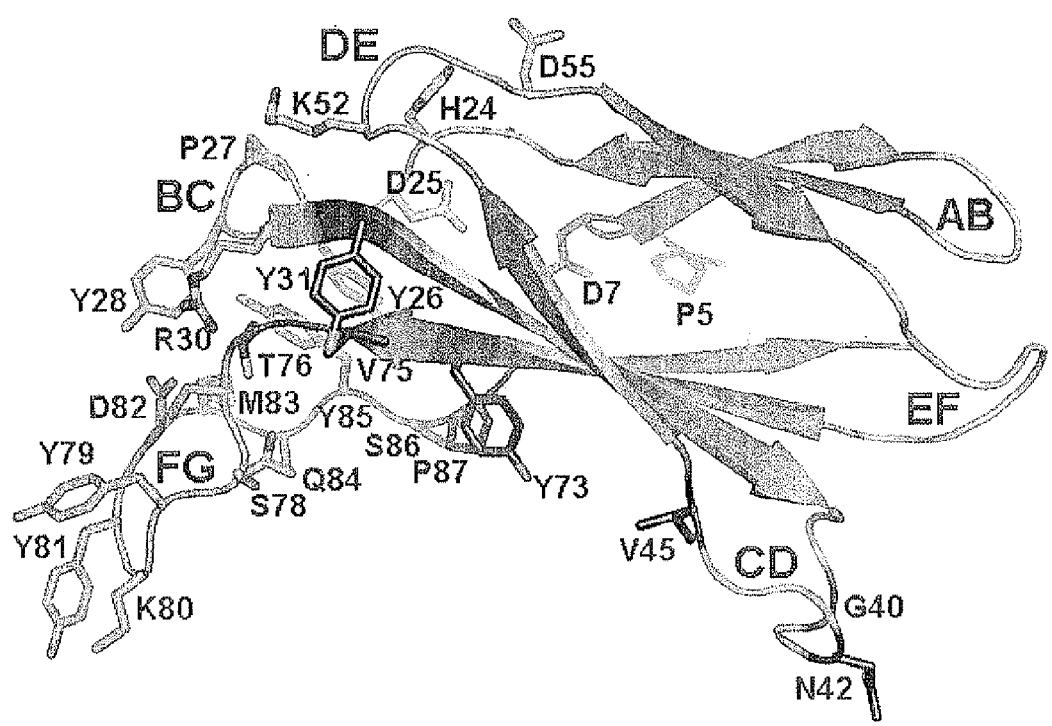
FIG. 4 shows the residues of Adnectin 1454B08 involved in contacts with IL-23. The Adnectin backbone is shown as a cartoon with β-strands colored red, non-repetitive secondary structure colored orange, and diversified loops colored magenta. Residues involved in contacts from the diversified loops are shown with magenta carbon atoms, blue nitrogen atoms and red oxygen atoms. Residues involved in contacts from the remainder of the Adnectin are shown with black carbon atoms and black regions on the secondary structure cartoon. Note that residues from the N-terminal region, the C-strand, the CD loop on the opposite side of the molecule from the diversified loops, the E-strand and the F-strand make contacts with IL-23. Figure produced with PyMol (DeLano, 2002).

The principal interactions occur through the FG (~540 Å$^2$) and BC (~300 Å$^2$) loops, but most segments of secondary structure have at least some surface area buried by the interaction. The following residues from the Adnectin are found to contact IL-23: N-terminal region: Pro5, Arg 6, Asp 7, BC-loop: Glu 23, His 24, Asp 25, Tyr 26, Pro 27, Tyr 28, Arg 30, C-strand: Tyr 31; CD-loop: Gly 40, Asn 42, Val 45; F-strand: Tyr 73, Val 75; FG-loop: Thr 76, Ser 77, Ser 78, Tyr 79, Lys 80, Tyr 81, Asp 82, Met 83, Gln 84, Tyr 85, Ser 86, Pro 87 (FIG. 4). Four points stand out from this list. First, the number of interacting residues is large and they come from many of the β-strands and loops. Second, contacts between the diversified DE-loop and IL-23 are absent. Third, the large number (7) of tyrosine residues involved in the interaction. The frequent occurrence of tyrosine has been observed for antibodies interacting with antigens (Padlan, "On the nature of antibody combining sites: Unusual structural features that may confer on these sites an enhanced capacity for binding ligands", *Proteins: Structure, Function and Genetics*, 7:112-124 (1989); Mian, "Structure, Function and Properties of Antibody Binding Sites", *J. Mol. Biol.*, 217:133-151 (1991); Kossiakoff et al., "Understanding mechanisms governing protein-protein interactions from synthetic binding interfaces", *Curr. Opin. Struct. Biol.*, 18:499-506 (2008); Koide et al., "The importance of Being Tyrosine: Lessons in Molecular Recognition from Minimalist Synthetic Binding Proteins", *ACS Chem. Biol.*, 4:325-334 (2009)), and is presumably due to the relatively low loss of entropy due to relatively few dihedral angles that become immobilized compared to large surface area that tyrosine residues are able to contribute, which amounts to a total of ~420 Å$^2$ in this case. Fourth, a large number (9) of non-diversified residues are involved in direct interactions with IL-23. Residues in this fourth category include 2 of the 7 Tyr residues and residues at the N-terminus. Although electron density is interpretable for only part of the N-terminus, it is clear that the N-terminus does not point in the direction of the BC, DE, and FG loops as it does in the wild-type $^{10}$Fn3, but rather reverses direction and points towards the opposite end of the molecule. This change of orientation prevents the N-terminus from colliding with IL-23 in the tight confines at the junction between the p40 and p19 subunits.

Interleukin-23 Competitive ELISA

Adnectin variants were tested by ELISA for their ability to bind IL-23 in a manner that was competitive with the binding site of the native IL-23 receptor (IL-23R). Recombinant human IL-23R-Fc (R&D Systems, Minneapolis, Minn.) was coated overnight at 4° C. on a NUNC® Maxisorp plate (Thermo Fisher Scientific, Denmark) with 50 µL at 4 µg/mL in PBS. All washing was performed with PBST (PBS with 0.05% (w/v) Tween) using an automated plate washer (Biotek, Vt.). OptEIA buffer (BD Bioscience, CA) was used as block and assay diluent. Adnectin dilutions ranging from 200 nM to 28 pM were pre-incubated with 1 nM IL-23 for an hour before transferring to blocked IL-23R-Fc coated plates for 30 minutes. Bound IL-23 was detected via anti-IL-23 (GeneTex, CA) and anti-mouse-HRP (R&D Systems, MN) followed by TMB (3,3',5,5'-tetramethylbenzidine) (BD Bioscience, CA) addition. Typical development time was 10 minutes. Percent inhibition was calculated by using a known IL-23 Adnectin neutralizing standard to define 100% inhibition and a non-binding Adnectin standard as the negative control. IC50s were generated from the average of four runs with an in-house curve fitting application.

Tyr 28, Tyr 73, Tyr 81 and Pro 87 were the four key amino acids mutated to alanine to demonstrate that we could predict energetically important residues. The tyrosine residues all have greater that 75% of their surface area buried at the IL-23 interface and Pro 87 has about 70% of its surface buried at the interface. Energetics calculations suggested that mutation to alanine at these positions would decrease binding. This proved to be the case for Tyr 28, Tyr 81, and Pro 87 but not for Tyr 73, which had little effect when mutated to alanine (Table 6).

TABLE 6

IL-23 IC50

| Mutation | Secondary Structural Element | IC50 | Activity (parent/mutant) | ΔInteraction Energy |
| --- | --- | --- | --- | --- |
| Parent | | 1.0 | 1 | |
| Y28→A | BC loop | 13 | 0.08 | 10 |
| Y73→A | F strand | 0.65 | 1.5 | 5 |
| Y81→A | FG loop | 35 | 0.03 | 7 |
| P87→A | FG loop | 8.3 | 0.1 | 2 |
| T35→N | C strand | 1.7 | 0.6 | 0 |
| T35→Q | C strand | 1 | 1 | −2 |
| T35→E | C strand | 0.6 | 1.7 | −6 |
| T35→D | C strand | 49 | 0.02 | −7 |
| V45→N | D strand | 0.54 | 1.8 | 1 |
| V45→Q | D strand | 0.34 | 2.9 | 0 |
| V45→E | D strand | 0.51 | 1.9 | −6 |
| V45→D | D strand | 0.83 | 1.2 | −6 |
| Y73→N | F strand | 1.2 | 0.8 | 2 |
| Y73→Q | F strand | 0.26 | 3.8 | 3 |
| Y73→R | F strand | 1.2 | 0.8 | −2 |
| V75→Y | F strand | 2.2 | 0.4 | −1 |
| V75→Q | F strand | 2.3 | 0.4 | 0 |
| V75→K | F strand | 5.7 | 0.2 | −1 |

Tyr 28 is located in the center of the BC-loop and forms significant contacts with amino acids that are at the terminus of the IL-23 p19 domain A-helix, e.g., edge-to-face interactions with Trp 26 and His 29. Similarly, Tyr 81 which is located in the center of the FG-loop has significant contacts with the IL-23 p40 subunit, e.g., Ser 204. Pro 87, which is located at the C-terminus of the FG-loop, may be required for retaining the FG-loop conformation and contacts residues Gly 100 and Pro 101 from the IL-23 p40 subunit. Tyr 73 is predicted to contribute only ~6 kcal to the interaction compared to Tyr 28 and Tyr 81, which contribute ~16 and ~13, respectively, and in the minimized structure the side chain forms a hydrogen bond with IL-23 p40 subunit Lys 99 carbonyl oxygen.

Effects of Site Directed Mutations

While alanine mutagenesis highlights contributions made by the functional group for each side chain replaced, substitution with other amino acids may be used to gain insights into new intermolecular interactions. We also attempted to find sites on 1454B08, where we could enhance the binding activity by the addition of new contacts. Most of these mutations changed the activity insignificantly. However, one that was predicted to be favorable, Thr35→Asp, drastically reduced the activity. On the other hand, Tyr 73→Gln yielded a modest increase in activity. By the combination of alanine mutagenesis and energetics calculations, we have been able to define a minimal energetic paratope for 1454B08 as consisting of at least Tyr 28 from the BC loop, Tyr 81 from the FG loop, and Pro 87, a non-diversified residue at the C-terminal end of the FG-loop.

Comparison of the Structures of 1454B08 with [10]Fn3

Structural comparisons show that of the wild-type molecule ([10]Fn3; 1FNF residues 1416-1509) has a very similar topology to that of 1454B08, when the latter is bound to its target molecule (FIG. 5), including an excellent overlay of the core β-sheet and two of the three loops (AB and DE) distal from those that are diversified (FIG. 5A, right side). All three diversified loops, BC, DE, and FG loops of 1454B08 are identical in length to the wild-type and in this structure the short DE loop shows minimal variation. On the other hand, the BC loop shows more variation when compared to the [10]Fn3 structure. The largest variations are in the FG loop, where, in the 1FNF crystal structure, the native ROD motif is involved in a crystal contact and that contact is likely responsible for its orientation in that structure. In 1454B08 the FG loop adopts a different conformation when bound to IL-23. Finally, it should be noted that the N-terminus is flexible in Adnectins. In [10]Fn3, the position is dictated by the link to [9]Fn3. On the other hand, the N-terminus of 1454B08 is folded away compared to [10]Fn3 N-termini presumably to avoid collision with IL-23.

---

We claim:

1. A polypeptide comprising a fibronectin type III tenth domain ($^{10}$Fn3) amino acid sequence of SEQ ID NO:1, wherein the N-terminal region prior to the A strand binds IL-23 and wherein the polypeptide further comprises Tyr 26, Tyr 28, Asp 82 and Tyr 85.

2. The polypeptide of claim 1 wherein N-terminal amino acids Pro 5, Arg 6 and Asp 7 bind to IL-23.

3. The polypeptide of claim 1 wherein the $^{10}$Fn3 binds IL-23 with a $K_D$ of less than 500 nM.

4. The polypeptide of claim 3 wherein the amino acid sequence comprises the sequence shown in SEQ ID NO: 32.

* * * * *